(12) United States Patent
Ahmad et al.

(10) Patent No.: US 7,417,013 B2
(45) Date of Patent: *Aug. 26, 2008

(54) WARMING AND NONIRRITATING LUBRICANT COMPOSITIONS AND METHOD OF COMPARING IRRITATION

(75) Inventors: Nawaz Ahmad, Monmouth Junction, NJ (US); Ying Sun, Belle Mead, NJ (US); Shun Y. Lin, Plainsboro, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 437 days.

This patent is subject to a terminal disclaimer.

(21) Appl. No.: 10/696,939

(22) Filed: Oct. 30, 2003

(65) Prior Publication Data

US 2004/0138074 A1  Jul. 15, 2004

Related U.S. Application Data

(63) Continuation-in-part of application No. 10/697,353, filed on Oct. 30, 2003, now abandoned, and a continuation-in-part of application No. 10/697,838, filed on Oct. 30, 2003, now abandoned, and a continuation-in-part of application No. 10/389,871, filed on Mar. 17, 2003, now Pat. No. 7,285,517, and a continuation-in-part of application No. 10/390,511, filed on Mar. 17, 2003, and a continuation-in-part of application No. 10/137,509, filed on May 1, 2002, now Pat. No. 7,005,408.

(51) Int. Cl.
*C10M 104/34* (2006.01)

(52) U.S. Cl. .................. 508/463; 508/505; 508/583; 424/400; 424/401

(58) Field of Classification Search ............... 508/463, 508/505, 583; 424/400, 401
See application file for complete search history.

(56) References Cited

U.S. PATENT DOCUMENTS

| | | |
|---|---|---|
| 4,110,426 A | 8/1978 | Barnhurst et al. |
| 4,232,003 A | 11/1980 | Posthuma et al. |
| 4,233,876 A | 11/1980 | Leahy et al. |
| 4,347,237 A | 8/1982 | Evenstad et al. |
| 4,636,520 A | 1/1987 | Umio et al. |
| 4,720,507 A | 1/1988 | Wiebe |
| 4,863,725 A | 9/1989 | Deckner et al. |
| 4,950,475 A | 8/1990 | Vishnupad et al. |
| 4,981,686 A | 1/1991 | Hardy |
| 5,002,938 A | 3/1991 | Wang et al. |
| 5,208,031 A | 5/1993 | Kelly |
| 5,225,191 A | 7/1993 | De Labbey |
| 5,236,609 A | 8/1993 | Smith et al. |
| 5,270,032 A | 12/1993 | Pollock et al. |
| 5,349,149 A | 9/1994 | Shiraki et al. |
| 5,393,528 A | 2/1995 | Staab |
| 5,512,289 A | 4/1996 | Tseng et al. |
| 5,513,629 A | 5/1996 | Johnson |
| 5,527,534 A | 6/1996 | Myhling |
| 5,529,782 A | 6/1996 | Staab |
| 5,595,980 A | 1/1997 | Brode et al. |
| 5,599,551 A | 2/1997 | Kelly |
| 5,658,583 A | 8/1997 | Zhang et al. |
| 5,696,164 A | 12/1997 | Sun et al. |
| 5,709,849 A | 1/1998 | Ito et al. |
| 5,840,744 A | 11/1998 | Borgman |
| 5,885,591 A | 3/1999 | Ahmad et al. |
| 5,895,658 A | 4/1999 | Fossel |
| 5,902,593 A | 5/1999 | Kent et al. |
| 5,976,561 A | 11/1999 | Kent et al. |
| 5,980,875 A | 11/1999 | Mousa |
| 5,980,924 A | 11/1999 | Yamazaki et al. |
| 6,007,846 A | 12/1999 | Klar |
| 6,013,270 A | 1/2000 | Hargraves et al. |
| 6,019,782 A | 2/2000 | Davis et al. |
| 6,060,077 A | 5/2000 | Meignant |
| 6,139,848 A | 10/2000 | Ahmad et al. |
| 6,153,208 A | 11/2000 | McAtee et al. |
| 6,171,604 B1 | 1/2001 | Mousa |
| 6,190,680 B1 | 2/2001 | Sakurada et al. |
| 6,221,814 B1 | 4/2001 | Kaburagi et al. |
| 6,303,108 B1 | 10/2001 | Boulier et al. |
| 6,328,991 B1 | 12/2001 | Myhling |
| 6,338,855 B1 | 1/2002 | Albacarys et al. |
| 6,531,171 B2 | 3/2003 | Armand et al. |

(Continued)

FOREIGN PATENT DOCUMENTS

EP  0 027 730 A2  4/1981

(Continued)

OTHER PUBLICATIONS

Kutteh W H et al: "Vaginal lubricants for the infertile couple: effect on sperm activity" International Journal of Fertility, Allan Press, Inc. Kansas, US vol. 41, No. 4, 1996, pp. 400-404 XP000870083.

(Continued)

*Primary Examiner*—Edward J Cain

(57) ABSTRACT

This invention relates to substantially anhydrous warming, non-toxic and nonirritating lubricating compositions containing polyols and preferably an insulating agent. The invention also relates to methods of using such compositions for lubrication, administration of active ingredients and for preventing or treating dysmenorrhea.

11 Claims, 11 Drawing Sheets

U.S. PATENT DOCUMENTS

| | | | |
|---|---|---|---|
| 6,641,825 | B2 | 11/2003 | Scholz et al. |
| 6,664,296 | B1 | 12/2003 | Meignant |
| 6,706,674 | B2 | 3/2004 | Cincotta et al. |
| 6,939,569 | B1 | 9/2005 | Green et al. |
| 6,960,346 | B2 | 11/2005 | Shukla et al. |
| 7,005,408 | B2 * | 2/2006 | Ahmad et al. ............... 508/219 |
| 2002/0013304 | A1 | 1/2002 | Wilson et al. |
| 2002/0103414 | A1 | 8/2002 | Harrison et al. |
| 2003/0092754 | A1 | 5/2003 | Nishimuta et al. |
| 2003/0211161 | A1 | 11/2003 | Ahmad et al. |
| 2003/0232090 | A1 | 12/2003 | Ahmad et al. |

FOREIGN PATENT DOCUMENTS

| | | | |
|---|---|---|---|
| EP | 0027730 | A | 4/1981 |
| EP | 0 404 376 | A2 | 12/1990 |
| EP | 0 581 581 | A2 | 2/1994 |
| EP | 0 966 956 | B1 | 12/1999 |
| ES | 2 074 030 | B1 | 8/1995 |
| JP | 2-311408 | A | 12/1990 |
| JP | 2-311408 | R | 12/1990 |
| JP | 2001-335429 | A | 12/2001 |
| NZ | 235054 | A | 11/1992 |
| RU | 2155582 | C2 | 9/2000 |
| RU | 2180556 | C2 | 3/2002 |
| WO | WO 98/18448 | A | 5/1998 |
| WO | WO 98/18448 | A1 | 5/1998 |
| WO | WO 99/29301 | A3 | 6/1999 |
| WO | WO 01/05400 | A1 | 1/2001 |
| WO | WO 01/64176 | A1 | 9/2001 |
| WO | WO 02/087570 | A1 | 11/2002 |

OTHER PUBLICATIONS

PCT Search Report dated Aug. 21, 2003, for PCT Appl. No. PCT/US 03/13554.

PCT Search Report dated Aug. 21, 2003, for PCT Appl. No. PCT/US 03/13476.

Akin et al, "Continuous Low-Level Topical Heat in the Treatment of Dysmenorrhea. ", Obstetrics & Gynecology, vol. 97, No. 3, pp. 343-349 (Mar. 2001).

Fail et al, "General, Reproductive, Developmental, and Endocrine Toxicity of Boronated Compounds", Reproductive Toxicology, vol. 12, No. 1 (1998) pp. 1-18.

Package—BIORE Cleanse Self-Heating Mask (front, back and side).

Package—Oil of Love KAMASUTRA (front and back).

Sun, "Skin Absorption Enhancement by Physical Means: Ultrasound, and Electricity", Chapter 10 of Transdermal and Topical Drug Delivery System, edited by Ghosh et al, Interpharm Press, Inc., pp. 327-355 (1997).

U.S. Appl. No. 10/137,509, Ahmad et al.

U.S. Appl. No. 10/697,353, Ahmad et al.

U.S. Appl. No. 10/697,838, Ahmad et al.

PCT International Search Report dated Oct. 10, 2003, for corresponding PCT/US03/13475.

Remington: The Science and Practice of Pharmacy. Mach Publishing Company. 19th edition: 1995.

Water and Alcohol Mixtures and "The Amazing Air Bubble". Covenant Christian High School. 1999 http://htdconnect.com/~chargers/chem/seccwatalcohol.htm.

Digital photographs of package and package insert—Kamasutra Oil of Love.

EP Communication dated Jul. 25, 2005 for EP application 03731070.3.

* cited by examiner

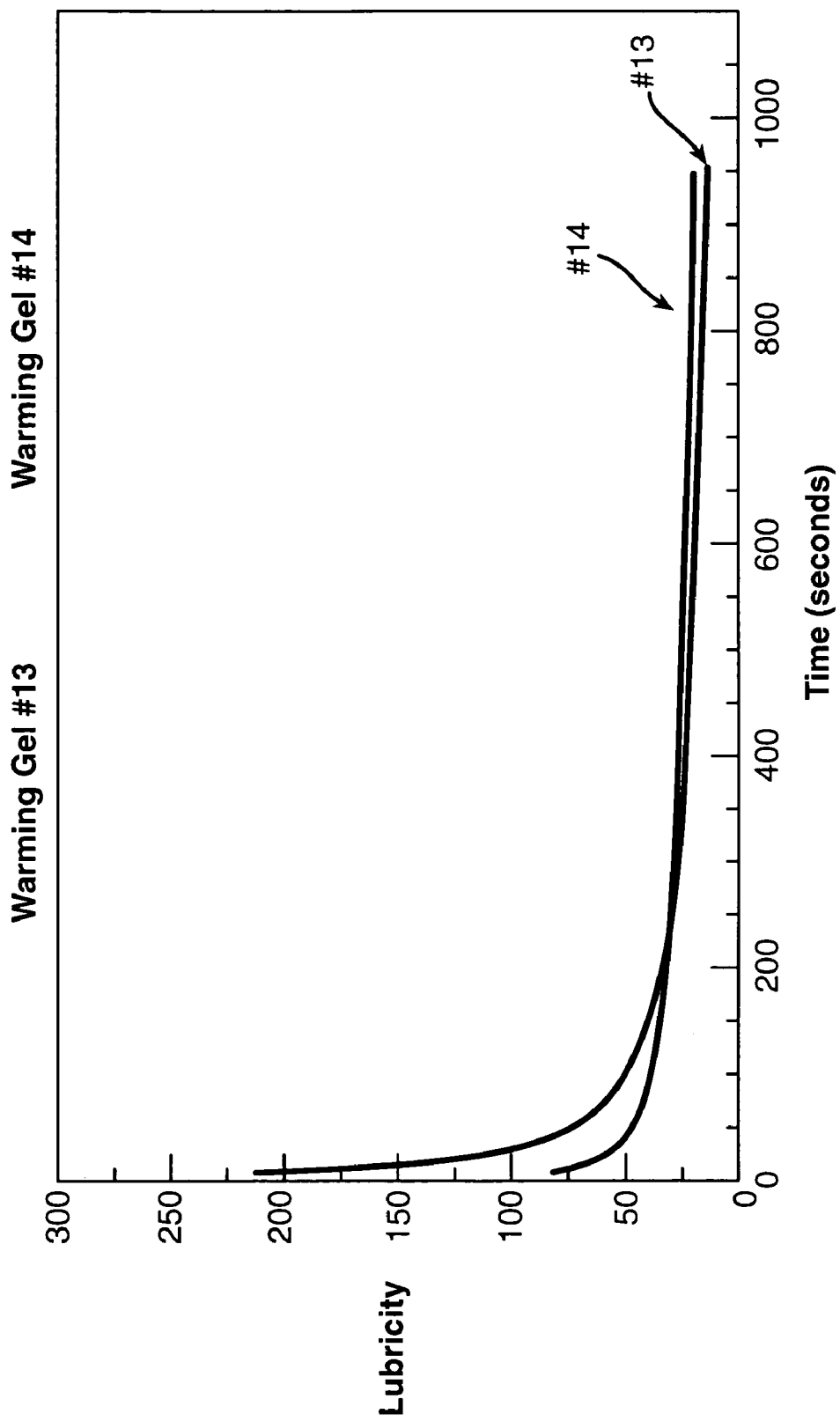

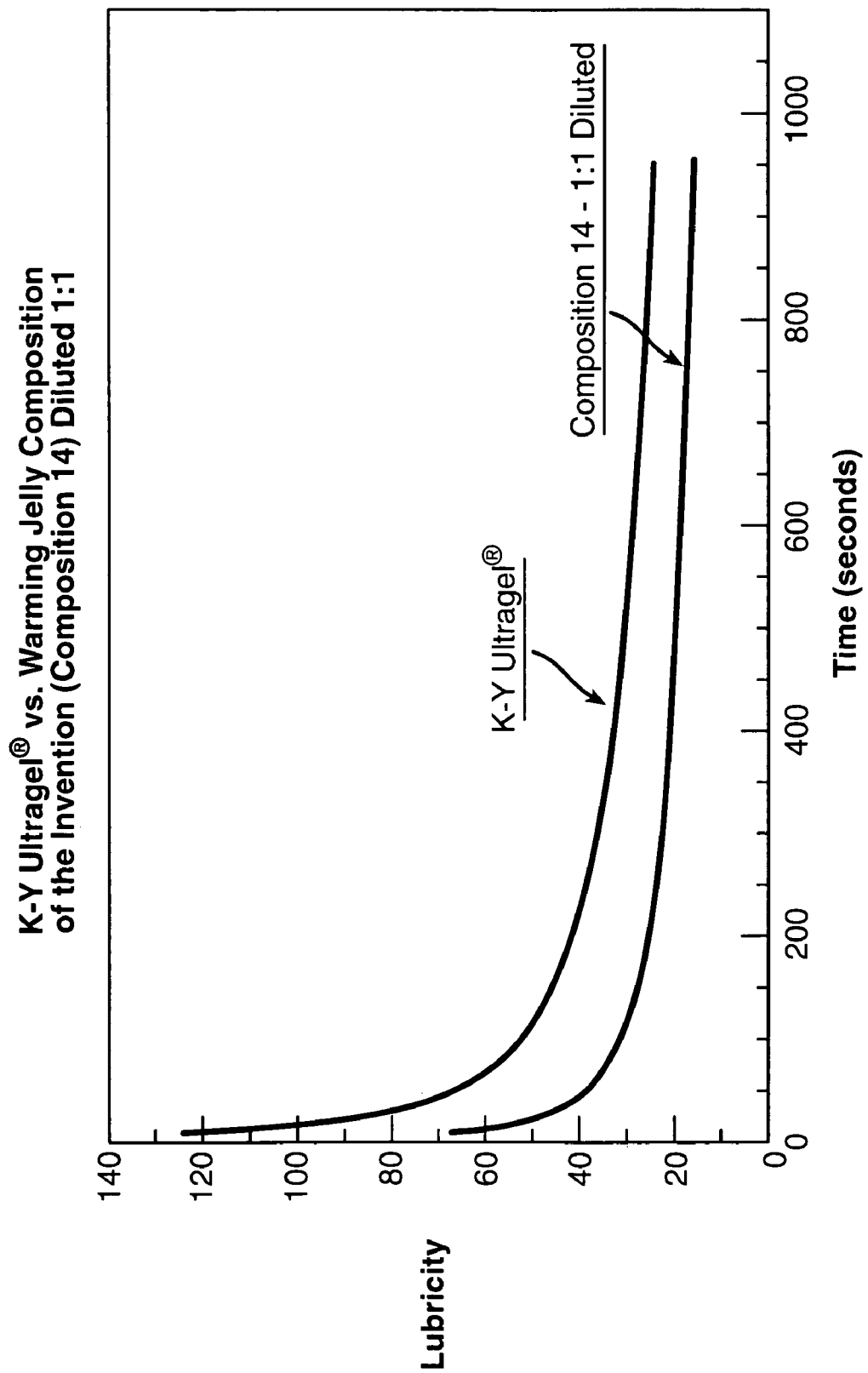

WARMING AND NONIRRITATING LUBRICANT COMPOSITIONS AND METHOD OF COMPARING IRRITATION

This application is a continuation-in-part of U.S. patent application Ser. No. 10/137,509, filed May 1, 2002, now U.S. Pat. No. 7,005,408, of U.S. patent application Ser. No. 10/389,871, filed Mar. 17, 2003 now U.S. Pat. No. 7,285,517, and of copending U.S. patent application Ser. No. 10/390,511, filed Mar. 17, 2003, and relates to U.S. patent application Ser. No. 10/697,353 and U.S. patent application Ser. No. 10/697,838 both filed on Oct. 30, 2003, and now abandoned, all of which are hereby incorporated herein by reference.

FIELD OF THE INVENTION

This invention relates to personal lubricant compositions that are warming and nonirritating when applied to the skin or mucous membranes, especially the vaginal or oral mucosa. In some embodiments, the compositions of this invention contain at least one polyol. This invention also relates to the method that can be used to test and compare the irritation of the compositions of this invention and other personal lubricants known to the art. Unlike previously-known compositions that use exothermic reactions to generate warmth or use irritants to convey a perception of warmth, the compositions of this invention use "heat of solution" to generate warmth. The feeling of warmth generated by the compositions of this invention is very pleasant and mild in comparison with previously-known compositions. The compositions of this invention are also more lubricating to tissue than previously-known warming compositions. Furthermore, the lubricity of the compositions of this invention increases upon dilution with water; the lubricity of previously-known aqueous compositions tends to decrease upon dilution with water. In actual use, therefore, the compositions of this invention will be considerably more lubricating than those previously known to the art.

The compositions of this invention are substantially anhydrous and contain one or more polyols. This invention also relates to the method that can be used to test and compare the irritation of the compositions of this invention and other personal lubricants known to the art.

BACKGROUND OF THE INVENTION

Humans are warm-blooded animals that maintain a constant body temperature of 98.6° F. (37° C.). Human skin and external organs have a very efficient circulatory and nervous system with the result that the human body can very quickly perceive changes in temperature. Personal lubricants and medicaments are usually applied to humans' mucous membranes at room temperature, i.e., between at 60° F. and 80° F. Because there is an appreciable difference in temperature between room temperature and human body temperature, users of such lubricants and medicaments perceive them to be quite cold. This feeling of cold can be quite uncomfortable for the user. From time to time, attempts have been made to develop products that overcome this perception of cold. When an individual applies personal lubricant or medicament such compositions to internal mucosal membranes, often an individual experiences an uncomfortable, cold feeling due to the difference in temperature between the body and the ambient temperature.

An appreciable number of personal lubricant compositions are known to the art. These compositions range from jellies to liquids to vaginal suppositories and vary from being aqueous to oils to silicone based. The majority of the compositions actually used today are aqueous jellies or aqueous liquids. Almost all personal lubricants known and available for use today are cold to touch, a feeling that can be uncomfortable.

A number of compositions are known to the trade or described in the literature that claim to impart a warming sensation upon application to the skin or mucosa. Some of these compositions use plant extracts which are irritating to the skin and mucous membranes and give a feeling or perception of warmth by virtue of their irritant action. Others claim to enhance blood flow in order to cause tissue warming. Still others are alleged to work on the principle of freezing point depression and are well suited for heating in a microwave or cooling in a refrigerator. There is one cosmetic composition rendered self-heating by inclusion of compound containing a boron-to-boron linkage, which reacts exothermally with water.

One category of warming compositions use plant extracts or agents, such as methyl salicylate, that are irritating to the skin or mucous membranes. For example, WO 97/02273A describes phosphate derivatives useful in oral and topical compositions to provide a perceived sensation of warmth. The compositions contain warming components such as vanillyl derivatives. The compositions also incorporate an additional warming agent, including ethanol, niacin, jambu, nicotinic acid, zingerone, vanillyl alcohol isopropyl ether, gingerol, methyl salicylate, shogaol, paradol, zingerone, capsaicin, dihydrocapsaicin, nordihydrocapsaicin homocapsaicin, tincture capsicum, eucalyptus oil.

JP2001335429 describes gel-like cosmetics that contain 40-75% by weight of polyethylene glycol, 20-55% by weight of glycerol and carboxyvinyl polymer. These compositions are used for generating heat for promoting blood circulation and metabolism in fatigue conditions and to provide warm feeling during shaving. One example of a composition known to the trade, Prosensual™, distributed by Lexie Trading, Inc., Fairlawn, N.J., contains plant extracts such as Cinnamon *cassia* (Cinnamon), *Zingiber officinalis* (Ginger), Mint, Sandalwood, Orange and Clove, which are all known to be skin irritants. Such a composition has the disadvantage of causing irritation to the mucosa, which can be problematic in relation to the vaginal or oral mucosa as irritation may promote the growth of unwanted bacteria and cause infection.

Another current composition, WET™ Heating Massage Oil, distributed by International, Valencia, Calif., uses Retinyl Palmitate (Vitamin A Palmitate), *Prunus amygdalis* (Prunes), Amara (Almond), *Persica gratissima* (Avocado Oil), Macadamia ternifulia Seed Oil, Kakeri Nut Oil, *Helianthus annus* (hybrid Sunflower), *Cannabis sativa* (Hemp) Seed Oil and Aloe vera. Most of these ingredients are known irritants that are not suitable for use on mucous membranes.

One category of warming compositions use plant extracts or agents, such as methyl salicylate, that are irritating to the skin or mucous membranes. For example, WO 97/02273A describes phosphate derivatives useful in oral and topical compositions to provide a perceived sensation of warmth. The compositions contain warming components such as vanillyl derivatives. The compositions also incorporate an additional warming agent, including ethanol, niacin, jambu, nicotinic acid, zingerone, vanillyl alcohol isopropyl ether, gingerol, methyl salicylate, shogaol, paradol, zingerone, capsaicin, dihydrocapsaicin, nordihydrocapsaicin homocapsaicin, tincture capsicum, eucalyptus oil.

Another category of warming products utilize the mechanism of increased blood circulation. U.S. Pat. No. 5,895,658, entitled "Delivery of L-Arginine to Cause Tissue Warming, Sustained Release of Nitric Oxide to treat effects of Diabetes, Stimulate Hair Growth and Heal Wounds," describes a preparation for producing enhanced blood flow in tissues thus causing beneficial effects, such as warming cold tissues of hands and feet.

Yet another category of warming products uses inorganic compounds to create exothermic reactions resulting in the evolution of heat. WO 200260408 A1, for example, relates to anhydrous cosmetic hair care compositions containing inorganic salts such as sodium sulfate, calcium sulfate, aluminum sulfate, calcium chloride, magnesium chloride or calcium oxide, or magnesium sulfate. Upon mixing with water, these compositions generate heat.

KR20010227018 describes exothermic cosmetic containing active zeolite compositions that promote blood circulation and metabolism by giving warm-sense to the skin. Active zeolite contains ethoxylated alcohol. JP63159490A relates to exothermic cosmetic compositions especially for softening hair containing reducing agents such as sodium sulphite, sodium thiosulphate, sodium pyrosulphite or sodium hydrogen sulphite and an oxidizing agent such as sodium bromate, potassium bromate or sodium perbromate.

EP2001306347 refers to compositions for use in preparing hair for shaving. The compositions contain at least one substance that undergoes a discernible chemical change when mixed during shaving. The substance changes temperature, emits a scent or undergoes oxidation, hydration, an acid-base reaction or an exothermic reaction.

Another category of heat-producing products uses mechanisms other than the three aforementioned categories. US 20020142015 A1 and JP 2002179517 A describe warming compositions for cosmetics, toiletries, bath additives and pharmaceuticals that contain a cooling agent and a specific p-hydroxybenzaldehyde derivative. The use of this p-hydroxybenzaldehyde cooling agent is intended to product a warming effect for a longer duration. FR2810240 A1 describes cosmetic compositions containing a component that can absorb or release heat thereby providing a cooling and refreshing effect during exposure to heat or a warming effect during exposure to cold, such as a combination of long chain hydrocarbon compounds that can absorb thermal energy and store or exchange heat. U.S. Pat. No. 3,632,516A describes a self-heating lather that is rapidly heated by hydrogen peroxide via a thiosulphredox reaction.

Another category of warming products utilize the mechanism of increased blood circulation. U.S. Pat. No. 5,895,658, entitled "Delivery of L-Arginine to Cause Tissue Warming, Sustained Release of Nitric Oxide to treat effects of Diabetes, Stimulate Hair Growth and Heal Wounds," describes a preparation for producing enhanced blood flow in tissues thus causing beneficial effects, such as warming cold tissues of hands and feet.

U.S. Pat. No. 5,513,629 entitled "Microwavable Heat Releasing and Absorbing Compositions and Container, Pliable Gel Comprising Humectant, Freezing Point Depressant, Gel Sealer, Polyacrylamide Absorbent, Corn Starch Binder, Mineral Oil and Plasticizers, Durability, Efficacy" describes compositions that have a high vapor points and are, therefore, suited for heating in a microwave oven or cooling in a freezer and placement in a suitable container or vinyl package, such as a hot-and-cold pack, but not for human consumption or use.

However, none of the foregoing compositions are actually "warm", or at a relatively higher temperature than the ambient temperature of the product or the surrounding environment.

U.S. Pat. No. 4,110,426, entitled "Method of Treating Skin and Hair with a Self Heated Cosmetic, Organic Boron-Oxygen-Boron Compounds" describes non-aqueous compositions such as shaving creams, that are rendered self-heating by including therein a compound containing at least one boron-oxygen-boron linkage, such as triethoxyboroxine. The boron-containing compound reacts exothermally with water or other protic material to increase temperature. Such compositions are not suitable for vaginal or oral use due to the potential toxicity of boron-containing compounds to the human reproductive system (Fail P A, et al., general, reproductive, developmental, and endocrine toxicity of boronated compounds., Reprod toxicol 12: 1, 1-18, January-February, 1998).

Physical energy forms have been utilized to enhance material transport across a membrane for therapeutic purposes. Such energy forms include electricity, ultrasound and thermal energy (e.g., heat-assisted drug delivery), (reviewed by Sun, in "Skin Absorption Enhancement by Physical Means: Heat, Ultrasound, and Electricity", *Transdermal and Topical Drug Delivery Systems*, Interpharm Press, Inc., 1997, pages 327-355). Local heating of a drug delivery system or formulation, as well as the skin or mucosal tissues, not only increases thermodynamic energy of drug molecules and membrane permeability to facilitate drug movement across a barrier membrane, it improves blood circulation in the tissue to expedite drug removal from the local tissue into the systemic circulation. Both processes leads to an enhanced absorption of the drug. Experimental evidence demonstrates that low-level heating (i.e., a tissue temperature of less than about 42° C.) significantly enhances percutaneous drug absorption.

U.S. Pat. No. 5,658,583 describes a heat-generating apparatus for improved dermal permeation of pharmaceuticals. The apparatus includes a thin drug formulation reservoir and a heat-generating chamber of oxidation reaction separated by a non-permeable wall. The drug formulation reservoir houses a predetermined amount of a formulation containing pharmaceutical agents. The heat-generating/temperature-regulating chamber includes a heat-generating medium consisting of carbon, iron, water and/or salt which is activated upon contact with oxygen in the air. However, a complicated heating device such as this is not suitable for use in the vaginal or oral cavity for obvious safety concerns.

Locally applied heat (such as an abdominal heating patch) has also been used to treat dysmenorrhea, or menstrual cramps, with demonstrated efficacy (Akin M D et al., Continuous low-level topical heat in the treatment of dysmenorrhea., *Obstet Gynecol* 97: 3, 343-9, March, 2001).

U.S. Pat. No. 6,019,782 describes disposable thermal body pads with heat generation via an oxidation reaction intended for relieving menstrual pain when applied onto the abdominal skin. There is currently a commercial product in the U.S. market for dysmenorrhea treatment based on abdominal heating, ThermaCare® Air-Activated Heatwraps, Menstrual Cramp Relief patches manufactured by Procter & Gamble (Cincinnati, Ohio). However, there are no products or description of internal localized heating to treat dysmenorrhea.

SUMMARY OF THE INVENTION

The compositions and methods of this invention relate to warming lubricant compositions that are non-toxic and non-irritating and that can be used as personal lubricants designed to come into contact with the skin or mucosa. When mixed with water, the compositions of this invention increase in temperature or generate warmth. This has a soothing effect on the tissues to which these compositions are applied.

The compositions of this invention may be applied to the skin or mucous membranes, preferably the vaginal or oral mucosa. The compositions of this invention are preferably substantially anhydrous and preferably contain at least one polyol.

We theorize that, when the polyols contained in the compositions of this invention come into contact with water or body moisture in humans, they react with the ambient water molecules to cause an increase in temperature or generate warmth, thus having a soothing effect on the tissues to which these compositions are applied.

Surprisingly, and contrary to the general belief that polyols in compositions are irritating to the mucosa, compositions of this invention containing such polyols have been found to be non-irritating. In fact, these compositions are very mild to the skin and mucous membranes. The compositions of this invention are soothing when applied to oral mucous membranes and may function to relieve minor irritation of the mouth and throat.

The combination of polyols in the compositions of this invention may also be used as a vehicle to solubilize otherwise insoluble drugs, including, but not limited to, antifungals, antibacterials, antivirals, analgesics, anti-inflammatory steroids, contraceptives, local anaesthetics, hormones and the like.

The compositions of this invention optionally also preferably contain an insulating agent which functions to preserve the temperature increase by maintaining the heat within the composition after it has been applied to the skin or mucosa. More preferably, honey may be utilized as an insulating agent.

This invention also relates to methods of enhancing intimacy by applying the compositions of this invention topically as a personal lubricant or intimacy-enhancing composition. The methods of this invention may also relate to use of the compositions of this invention to mucosal surfaces, including vaginal and buccal surfaces, as a massage medium and in other uses as set forth below.

BRIEF DESCRIPTION OF THE DRAWINGS

FIG. 10 is a graph comparing the Lubricity vs Time (seconds) of the composition of Warming Gel 13 vs. Warming Gel 14.

FIG. 11 is a graph comparing the Lubricity vs Time (seconds) of the composition of K-Y® Ultragel vs. Composition 14.

DETAILED DESCRIPTION OF THE PREFERRED EMBODIMENTS

Figure 1:
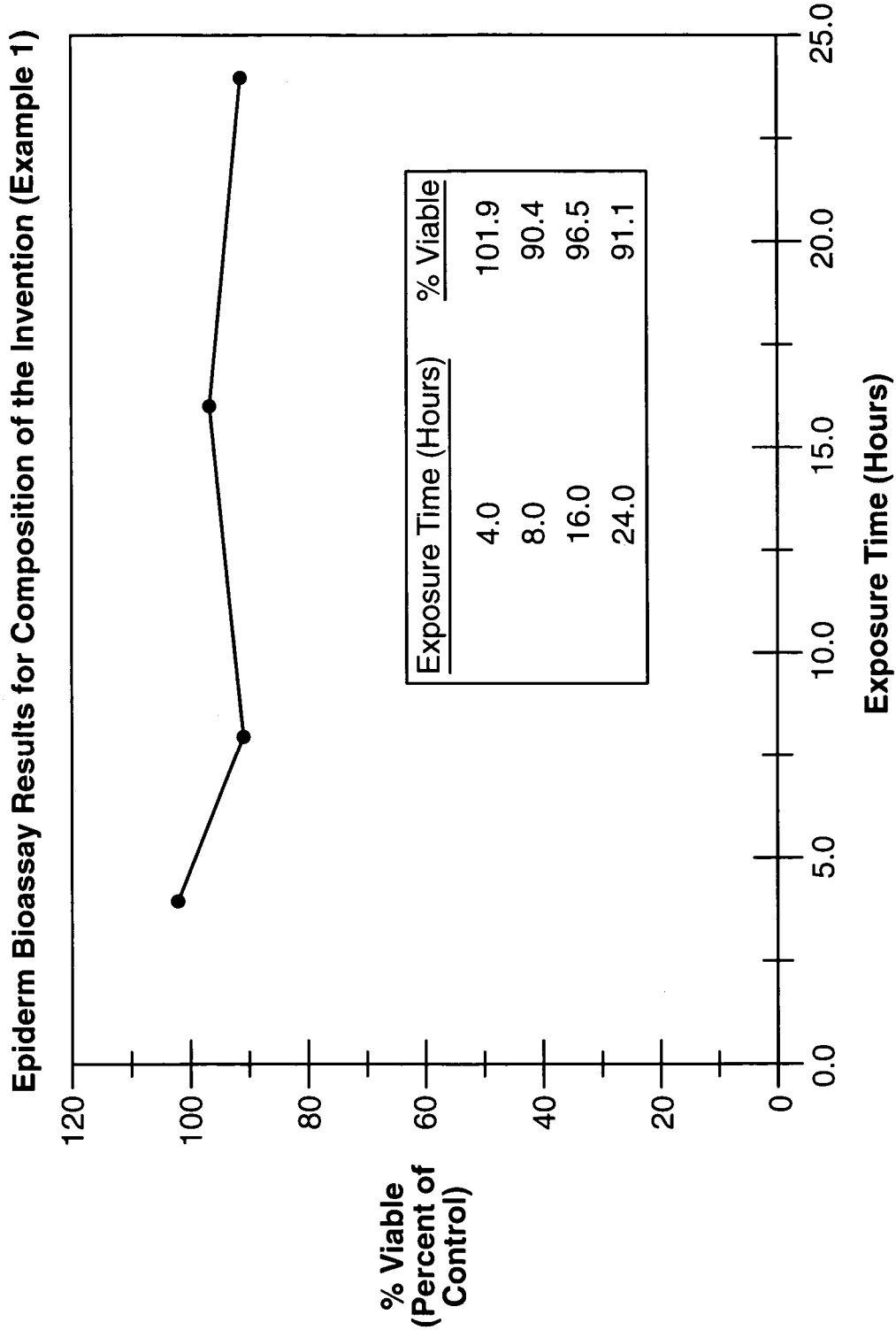
FIG. 1 is a graph depicting the % viable Epiderm cells vs Exposure Time using the composition of Example 1.

The compositions of this invention are substantially anhydrous, preferably containing less than about 20% water, more preferably containing less than about 5% water and, most preferably, containing less than about 3% water.

Preferably, the compositions of this invention contain at least one polyol. Preferably, the polyol is a polyhydric alcohol, and more preferably, the compositions of this invention contain at least two polyhydric alcohols. Polyethylene glycol (hereinafter, "PEG") ethers may also be used, including PEG ethers of propylene glycol, propylene glycol stearate, propylene glycol oleate and propylene glycol cocoate and the like. Specific examples of such PEG ethers include PEG-25 propylene glycol stearate, PEG-55 propylene glycol oleate and the like. Preferably the polyhydric alcohol portion of the compositions of this invention one or more polyhydric alcohols such as alkylene glycols and others selected from the following group: glycerin, propylene glycol, butylene glycol, hexalene glycol or polyethylene glycol of various molecular weight and the like and/or combination thereof. More preferably, the compositions of this invention contain a polyethylene glycol; most preferably, the polyethylene glycol may be selected from the following group: polyethylene glycol 400 or polyethylene glycol 300. Polypropylene glycol of various molecular weights may also be used. PEGylated compounds such as peptide or protein derivatives obtained through PEGylation reactions may also be used. In addition, block copolymers of PEG's may be used, such as (ethylene glycol)-block-poly(propylene glycol)-block-(polyethylene glycol), poly(ethylene glycol-ran-propylene glycol) and the like. The compositions of this invention should contain polyols in an amount from about 80% to about 98% by weight of the composition.

The compositions of this invention may optionally and preferably also contain an insulating agent. More preferably, the insulating agent should be honey or esters of isopropyl alcohol and saturated high molecular weight fatty acids such as myristic or palmitic acid, e.g., isopropyl myristate and isopropyl palmitate. The insulating agent should be present in the compositions of this invention in an amount of from about 1% to about 5% by weight of the composition. However, other filler-type agents may be utilized that can assist in retaining heat, such as materials with high bulk properties or materials that raise resistance to heat loss, known to those of skill in the art. Such materials may include aluminosilicates (for example, clay, zeolites and the like), alkyl celluloses and other cellulose derivatives and other like materials know to those of skill in the art.

Surprisingly, the compositions of this invention actually increase in temperature upon exposure to moisture from the skin or mucosa, without causing undue irritation or harm to the skin or mucosal surfaces. This distinguishes them from previously-known products that merely conveyed the sensation of warming by causing irritation to the topical surface to which they were applied.

This warming characteristic is brought about by the exothermic release of energy generated upon exposing the compositions of this invention to water. As set forth below in Example 6, the amount of energy released by the compositions of this invention, and in turn the potential temperature increases, upon exposure to water may be calculated or measured in accordance with the procedures set forth therein. Preferably, the temperature increase of the compositions of this invention range from the minimum perceptible temperature increase to no more than would be perceived as a "burning" sensation to the skin or mucosa, thus causing irritation or insult to the skin or mucosa. Such a temperature might be about 40° F. or more.

Preferably, the amount of energy released (hereinafter, "Energy Release Index") by solubilizing the compositions of this invention is from about 11 to about 28 mJ/mg (milliJoules per milligram). The associated preferred temperature rise range is at least about 5° C. (about 9° F.). More preferably, the temperature increase is from about 7° C. or about 13° F. and no more than about 12° C. or about 22° F. Gel-type embodiments of the compositions of this invention preferably effect a temperature increase from at least about 13° F. upward, preferably up to about 31° F. Jelly-type embodiments of the compositions of this invention preferably effect a temperature increase from at least about 7° F. and may effect a temperature increase up to about 27° F. However, this range may vary depending upon the composition.

The compositions of this invention are unexpectedly self-preserving and may not require a preservative. However, a preservative may be added to impart an additional guarantee against microbial growth. A preservative may be selected from preservatives known to those of skill in the art, including, but not limited to, one or more of the following: methylparaben, benzoic acid, sorbic acid, gallic acid, propylparaben or the like. The preservative may be present in the compositions of this invention in an amount from about 0.01% to about 0.75% by weight of the composition.

The compositions of this invention may also preferably contain an ester. More preferably, the ester is a fatty acid ester. Most preferably, the ester may include, but is not limited to: isopropyl stearate, isopropyl myristate, isopropyl palmitate, isopropyl laurate and the like. Most preferably, the ester is isopropyl myristate.

The compositions of this invention may contain one or more water-soluble cellulose-derived polymers, gums, chitosans or the like. Such polymers contribute to the viscosity and bioadhesiveness of the compositions of this invention. Preferably, such cellulose-derived polymers are hydroxyalkylcellulose polymers. More preferably, the hydroxyalkylcellulose polymer is hydroxypropylcellulose or Klucel®, available commercially from Hercules Incorporated, Wilmington, Del.

The polyols used in the compositions of this invention are theorized to be useful as warming and heat-generating agents. Honey functions as an insulating agent, protecting the compositions from becoming too cold. The ester, preferably a fatty acid ester, functions as an emollient and lubricant. The cellulose polymer is useful as a viscosity building agent. The compositions of this invention are unique in that they lubricate, warm and soothe the tissues of the user, especially the oral and vaginal mucous membranes, without conveying a feeling of cold. Moreover, they are smooth and lubricating.

The compositions of this invention may be a liquid, a semi-solid, or a solid depending upon the particular intended use thereof. The compositions of this invention may also be formulated into soft or hard gelatin capsules, suppositories and impregnated into fabrics or polymers.

The compositions of this invention may be used as personal lubricants which convey a feeling of warmth. The feeling of warmth generated by the compositions of this invention is soothing to the skin or mucous membranes where they are applied. The compositions of the invention also possess a sweet and pleasant taste, which is of particular benefit when these compositions are used orally.

The compositions of this invention may also be used as personal moisturizers, which convey a feeling of warmth when applied to vaginal or oral mucosa. The feeling of warmth generated by the compositions of this invention is soothing to the skin or mucous membranes where they are applied. The compositions of this invention also possess a sweet and pleasant taste, which is of particular benefit when these compositions are used orally. This warming effect has been found to enhance intimacy and increase pleasure during intimate activities. Flavors and fragrances that enhance different senses and promote relaxation or intimacy may also be added to the compositions of this invention to enhance their effect, both in improving intimacy and in creating a feeling of relaxation. The compositions of this invention may also be used as a massage "oil" which imparts warming sensation to the skin as it is applied to the skin during massage.

The compositions of this invention may also be used as moisturizers which convey a feeling of warmth and relieve vaginal dryness or dry mouth. They may also be utilized to moisturize dry and scaly skin, and to provide an ameliorating effect for frostbite on extremities over-exposed to the cold.

The compositions of this invention may also be used as a vehicle to deliver medication or other treatment agents to biomembranes including, but not limited to, hormones, antimicrobial or antifungal agents and the like. The antifungal agents is preferably an azole or imidazole, including but not limited to, miconazole, econazole, terconazole, saperconazole, itraconazole, butaconazole, clotrimazole, tioconazole, fluconazole and ketoconazole, vericonazole, fenticonazole, sertaconazole, posaconazole, bifonazole, oxiconazole, sulconazole, elubiol, vorconazole, isoconazole, flutrimazole and their pharmaceutically acceptable salts and the like. Other antifungal agents may include an allylamine or one from other chemical families, including but not limited to, ternafine, naftifine, amorolfine, butenafine, ciclopirox, griseofulvin, undecyclenic acid, haloprogin, tolnaftate, nystatin, iodine, rilopirox, BAY 108888, purpuromycin and their pharmaceutically acceptable salts.

Another embodiment of the invention are compositions for vulvovaginal use containing one or more antibiotics. The antibiotic may be chosen from the group including, but not limited to, metronidazole, clindamycin, tinidazole, ornidazole, secnidazole, refaximin, trospectomycin, purpuromycin and their pharmaceutically acceptable salts and the like.

Another embodiment of the compositions of this invention include compositions for vulvovaginal use containing one or more antiviral agents. Antiviral agents may preferably include, but are not limited to, immunomodulators, more preferably imiquimod, its derivatives, podofilox, podophyllin, interferon alpha, reticolos, cidofovir, nonoxynol-9 and their pharmaceutically acceptable salts and the like.

Still other embodiments of the compositions of this invention are compositions that include one or more spermicides. The spermicides may preferably include, but are not limited to, nonoxynol-9, octoxynol-9, dodecaethyleneglycol monolaurate, Laureth 10S, and Methoxypolyoxyethyleneglycol 550 Laurate and the like.

Still other embodiments of the compositions of this invention are compositions containing antimicrobial agents. The antimicrobial agents may preferably include, but are not limited to, chlorohexidine gluconate, sodium polystyrene sulfonate, sodium cellulose sulfate, silver particles of micro- and sub-micrometer sizes, silver salts and other antibacterial agents known to the art.

Yet other embodiments of the compositions of this invention are compositions that may include local anesthetics. The local anesthetics may preferably include, but are not limited to, benzocaine, lidocaine, dibucaine, benzyl alcohol, camphor, resorcinol, menthol and diphenylhydramine hydrochloride and the like.

Compositions of the invention may also include plant extracts such as aloe, witch hazel, chamomile, hydrogenated soy oil and colloidal oatmeal, vitamins such as vitamin A, D or E and corticosteroids such as hydrocortisone acetate.

Another embodiment of the compositions and methods of this invention include compositions for vulvovaginal use containing one or more hormones for treating a decrease in estrogen secretion in the woman in need of estrogen replacement such as women with vaginal atrophy. The hormones may preferably include, but are not limited to, estrogen selected from the group consisting of estradiol, estradiol benzoate, estradiol cypionate, estradiol dipropionate, estradiol enanthate, conjugated estrogen, estriol, estrone, estrone sulfate, ethinyl estradiol, estrofurate, quinestrol and mestranol.

Another embodiment of the compositions and methods of this invention include compositions for vulvovaginal use containing one or more analgesics and/or nonsteroidal anti-inflammatory agents for treating dysmenorrhea or menstrual cramping. The analgesics and nonsteroidal anti-inflammatory agents may preferably include, but are not limited to, aspirin, ibuprofen, indomethacin, phenylbutazone, bromfenac, fenamate, sulindac, nabumetone, ketorolac, and naproxen and the like.

In another embodiment of the compositions and methods of this invention, the compositions may be useful for treating female sexual dysfunction by themselves as they may serve to increase blood flow to areas on which they are applied by increasing temperature thereon. Alternatively, they may contain agents known to those of skill in the art to treat female sexual dysfunction (including different aspects of female sexual dysfunction such as female sexual arousal disorder, hypoactive sexual desire disorder, orgasmic disorder and the like) as well as those that treat dyspareunia and/or vaginismus, or vulvodynia and to relieve pain upon intercourse. Such agents include hormones such as estrogen, prostaglandin, testosterone; calcium channel blockers, cholinergic modulators, alpha-adrenergic receptor antagonist, beta-adrenergic receptor agonists, camp-dependent protein kinase activators, superoxide scavengers, potassium channel activators, estrogen-like compounds, testosterone-like compounds, benzodiazepines, adrenergic nerve inhibitors, HMG-CoA reductase inhibitors, smooth muscle relaxants, adenosine receptor modulators and adenylyl cyclase activators. Such agents include phosphodiesterase-5 inhibitors and the like. The compositions of the invention may also contain vasodilators such as methyl nicotinate, histamine hydrochloride and very small non-irritating amounts of methyl salicylate.

Yet another embodiment of the compositions and methods of this invention include compositions for oral and vulvovaginal use relates to a method of enhancing the absorption of active agents from the applied compositions into the mucosal membrane by increasing the composition and mucosal tissue temperature via interaction of the polyols in the compositions and moisture on the mucosa and subsequently released heat.

Yet another embodiment of the compositions of this invention include compositions for vulvovaginal use relates to compositions and methods for preventing and/or treating dysmenorrhea by intravaginal warming or heating. Preferably, the composition heats the intravaginal area to a temperature preferably between about 37° C. and about 42° C., more preferably between about 38° C. and about 41° C. The compositions of invention for use in such a method may optionally contain active agents such as analgesics and nonsteroidal anti-inflammatory agents for dysmenorrhea treatment. The composition of the invention may be administered directly into the vagina by an applicator, or be impregnated into vaginal devices such as tampon for intravaginal applications.

The compositions of this invention may be manufactured as a coating of a tampon, or dispersing throughout the absorbent tampon material, or enclosed inside as a core of a tampon. The compositions of this invention for the warming tampon for preventing and/or treating dysmenorrhea preferably include a mixture of polyethylene glycols of various molecular weights produced by The Dow Chemical Company (Midland, Mich.) under the trade names of CARBOWAX SENTRY PEG 300 NF, CARBOWAX SENTRY PEG 400 NF, CARBOWAX SENTRY PEG 600 NF, CARBOWAX SENTRY PEG 900 NF, CARBOWAX SENTRY PEG 1000 NF, CARBOWAX SENTRY PEG 1450 NF, CARBOWAX SENTRY PEG 3500 NF, CARBOWAX SENTRY PEG 4000 NF, CARBOWAX SENTRY PEG 4600 NF, and CARBOWAX SENTRY PEG 8000 NF. The compositions of this invention for dysmenorrhea prophylaxis and treatment may contain one or more water-soluble cellulose-derived polymers and gums that form gels around the polyhydric alcohols such as glycerin, propylene glycol and polyethylene glycols thus reducing the dissolution of the polyhydric alcohols, prolonging the salvation heat release, and regulating the elevated temperature in the preferred temperature range.

This invention also relates to a method of determining and comparing relative amounts of irritation caused by particular sources using the EpiDerm™ Skin Model Assay as described in Example 1, such as compositions applied to skin or mucosal cells. The following Example 1 exemplifies the use of the method of this invention.

EXAMPLE 1

EpiDerm™ Skin Model Assay to Test Irritation of Lubricants

The method designated as EpiDerm™ Skin Model assay uses the epithelial cells derived from human skin as target cells and is commercially available from the MatTek Corporation. This assay is described in Berridge, M. V., et al. (1996) The Biochemical and Cellular Basis of Cell Proliferation Assays That Use Tetrazolium Salts. Biochemica 4: 14-19. The test materials are applied directly to the epithelial cell culture surface. This test has not previously been used for determining toxicity of test materials. The toxicity of the test material is evaluated on the basis of relative tissue viability vs time. The actual Tissue Viability is determined by NAD(P)H-dependent microsomal enzyme reduction of MTT in control and test article treated cultures. The negative control used in this assay was deionized water and the positive control was Triton X-100. The exposed cell cultures were incubated for 4, 8, 16 and 24 hours and assayed for reduction of MTT. The data is presented below in FIGS. 1 through 4 in the form of Relative Survival (relative MTT reduction) versus Exposure Time. Products with higher relative survival rates are less toxic or less irritating while the ones with lower survival rates are more toxic or irritating. The survival rate of four compositions of this invention ranged between about 81.3% and about 90.3%, indicating that the compositions of this invention are essentially non-irritating. Thus, preferably, at least about 50%, more preferably, at least about 80% and most preferably, at least about 90% of cells survive in this test when exposed to the compositions of this invention as measured by the Epiderm Skin Model Bioassay.

Figure 2:
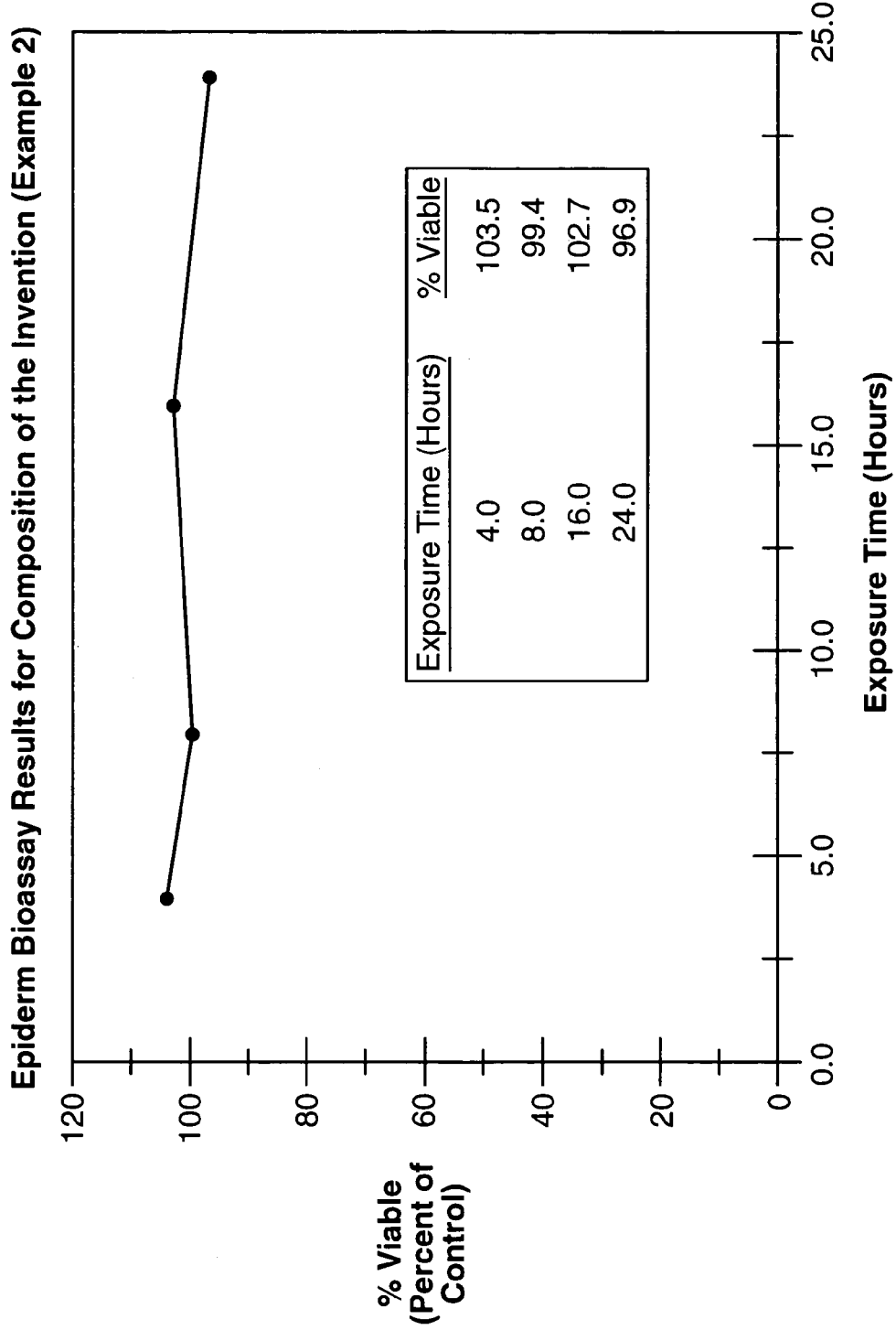
FIG. 2 is a graph depicting the % viable Epiderm cells vs Exposure Time using the composition of Example 2.
Figure 3:
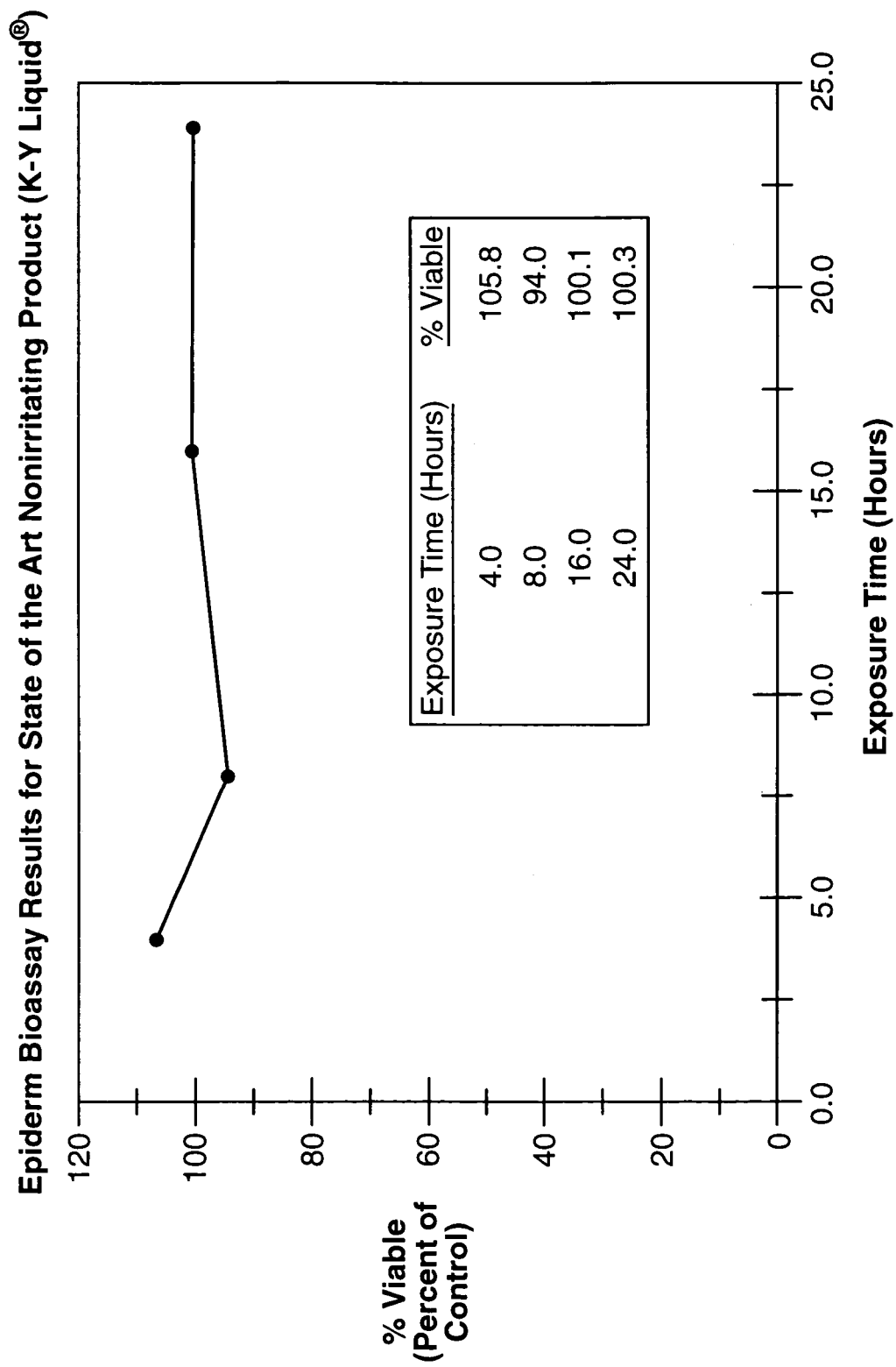
FIG. 3 is a graph depicting the % viable Epiderm cells vs Exposure Time using a State-of-the-Art non-irritating Product (K-Y Liquid®).

FIGS. 1 through 4 summarize the results of Epiderm Skin Model Bioassay. The data is plotted as % Viable Cells vs the Exposure Time ranging from 4 to 24 hours. FIGS. 1 and 2 represent the results for two compositions of this invention, Composition 1 and Composition 2 respectively. FIG. 3 represents the results of K-Y® Liquid that is an established personal lubricant on the market. K-Y® Liquid is established as safe and nonirritating in animal and human testing and long-term human use history. Results for K-Y® Liquid showed 100.3% viable cells after 24 hour of exposure (FIG. 3).

Figure 4:
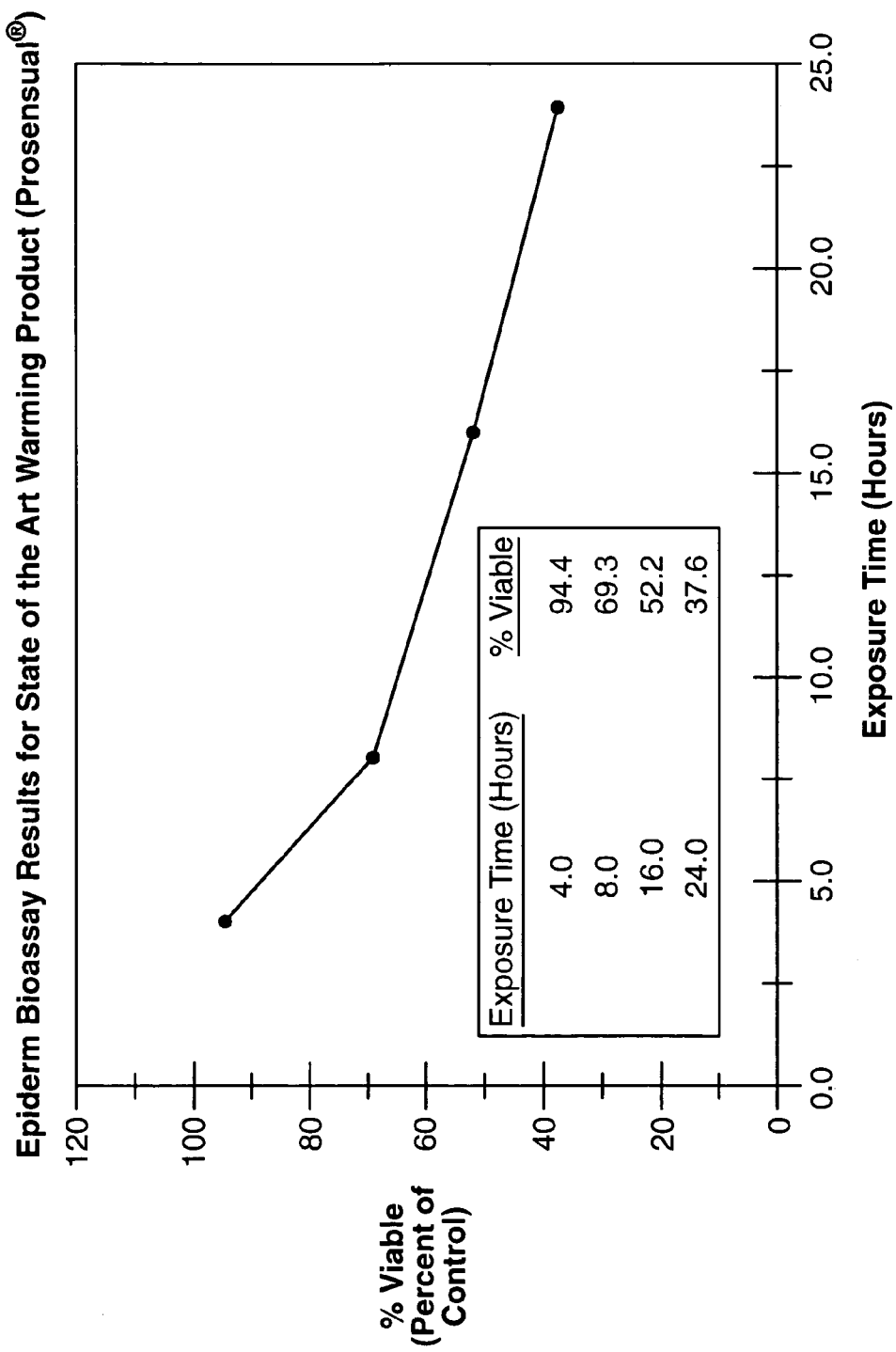
FIG. 4 is a graph depicting the % viable Epiderm cells vs Exposure Time using a State-of-the-Art warming Product (Prosensual®)

Example 1 of the invention (FIG. 1) and Example 2 of the invention (FIG. 2) showed 91.1% and 96.9% viable cells respectively. FIG. 4 shows the results of a warming composition known to the trade. This product uses plant materials like cinnamon, clove, ginger cloves and orange and others for a warming sensation. The results show only 37.6% viable cells after 24 hours of exposure to this product. This indicates that such compositions will be irritating to the skin and mucous membranes. Compositions 1 and 2 of this invention, with 91.1% and 96.9% viable cells respectively, will be practically nonirritating. Positive control (Triton X-100) has only 22.4% viable cells at the 8-hour interval.

EXAMPLE 2

Generation of Warmth

The compositions of this invention are anhydrous and contain one or more polyols. When combined with water, the polyols used in the compositions of this invention generate an increase in temperature that has a soothing effect on the tissues these compositions are applied. In actual use the compositions of the invention interact with the moisture of the vaginal or oral mucosa, thereby increasing the temperature or generating feeling of warmth.

The "Generation of warmth" data summarized in Table 1 below, was generated by mixing 20 ml of each of the ingredients in Composition 1 and Composition 1 of this invention with 20 ml of water. The temperature of the product and that of water were recorded before water was added to the product. After the addition of water the mixture was mixed for two minutes and the actual temperature was recorded. Glycerin, Propylene Glycol and Honey are the ingredients in Composition 1. It is clear from Table 1. that when mixed with water the temperature of the mixture rises by 9.0° F. for Glycerin, 13.5° F. for Propylene Glycol, 17.0° F. for Polyethylene Glycol 400 and 12.5° F. for composition Example 1 of this invention. The calculated rise in temperature for Composition 1, based on the rise in temperature and the % w/w quantity of each individual ingredient in the composition was 10.875° F. The actual recorded temperature rise for Composition 1. was 12.5° F. which is 1.625° F. higher than expected which indicates that there is an unexpected increase in temperature resulting from the combination of ingredients.

Generation of Warmth (Rise in Temperature ° F.)
Data by Mixing Equal Quantity of Each Product with Water

| Product Name | Temperature of the Product (° F.) | Temperature of Water (° F.) | Average Expected Temperature (° F.) | Actual Temperature (° F.) | Rise in Temperature (° F.) (Expected Minus Actual) |
|---|---|---|---|---|---|
| Glycerin Assay | 69.0 | 71.0 | 70.0 | 79.0 | 9.0 |
| Propylene Glycol Assay | 72.4 | 71.0 | 71.7 | 85.2 | 13.5 |
| Honey | 74.0 | 71.0 | 72.5 | 74.0 | 1.5 |
| K-Y Warming ® | 74.0 | 71.0 | 72.5 | 85.0 | 12.5 |
| Isopropyl Myristate | 75.0 | 74.1 | 74.5 | 75.2 | 0.7 |
| Polysorbate 60 | 70.9 | 74.1 | 72.5 | 83.1 | 10.6 |
| Polyethylene Glycol 400 | 72.0 | 71.0 | 71.5 | 88.5 | 17.0 |

Calculated Rise in Temperature: In order to determine the expected rise in temperature from each composition, the percentage of each component in such composition was multiplied by the temperature increase generated by such component alone to obtain its expected contribution to the temperature increase. These values were added together to calculate the total expected temperature rise. These values were then compared with the actual temperature rise generated by each composition. For example, the calculated rise in temperature generated by the "K-Y Warming®", composition in the table above was found as follows and compared with the actual temperature rise to determine the unexpectedly higher generation of warmth of the composition:

| | |
|---|---|
| Propylene Glycol (50% of 13.5) | = 6.75 |
| Glycerin (45% of 9.0) | = 4.05 |
| Honey (5% of 1.5) | = 0.075 |
| Total | 10.875 |

Difference: 12.5 − 10.875 = 1.625

EXAMPLE 3

Effect of Water Content on Generation of Warmth

On contact with moisture or water the heat of solution is responsible for the warming action of the compositions of this invention. There is a concern that accidental contamination with water or prolonged exposure to excessive moisture, the warming capacity of the product may be adversely effected. According to this example, water was added to compositions of this invention varying from about 1% to about 10% as outlined in Table 2 below. The contents were thoroughly mixed and the samples were allowed to stay at room temperature for 24 hour following which the generation of warmth was determined as outlined in the following paragraph. The results show that rise in temperature is proportionately decreased depending on the quantity of water added but there is still an 8.5° F. increase in temperature at about 10% water addition.

The results of this example are set forth in Table 2 below.

TABLE 2

Effect Of Water Content On Generation Of Warmth For K-Y Warm ®.

| Product Name | Temperature of the Sample (° F.) | Temperature of Water (° F.) | Average Expected Temperature (° F.) | Actual Temperature (° F.) | Rise in Temperature (° F.) (Expected Minus Actual) |
|---|---|---|---|---|---|
| No Water | 73.80 | 70.00 | 71.90 | 83.50 | 11.60 |
| 1% Water | 73.90 | 70.00 | 71.95 | 82.20 | 10.25 |
| 2% Water | 72.30 | 70.00 | 71.95 | 81.70 | 9.85 |
| 3% Water | 72.30 | 70.00 | 71.15 | 80.40 | 9.25 |
| 4% water | 72.20 | 70.00 | 71.10 | 80.70 | 9.60 |
| 5% Water | 71.60 | 70.00 | 70.80 | 80.40 | 9.60 |
| 6% Water | 71.60 | 70.00 | 70.80 | 80.40 | 9.60 |
| 7% Water | 71.50 | 70.00 | 70.75 | 80.20 | 9.45 |
| 8% Water | 71.60 | 70.00 | 70.80 | 80.20 | 9.40 |
| 9% Water | 70.90 | 70.00 | 70.45 | 79.50 | 9.05 |
| 10% Water | 70.50 | 70.00 | 70.25 | 79.00 | 8.50 |

EXAMPLE 4

Perception of Warmth in Human Use

A Human Use Study was conducted with 246 subjects. The data generated by this study are summarized below in Table 2. The subjects were asked to use compositions of this invention. They were asked three questions regarding the perception of warmth while using the product, as follows:
1. Does it warm on contact?
2. Does it feel warm?
3. Does it not feel cold?

The subjects were asked to register their response as Excellent, Very Good, Good, Fair and Poor. The positive responses are summarized in Table 2.

TABLE 3

PERCEPTION OF WARMTH IN HUMAN USE STUDY WITH 246 HUMAN SUBJECTS USING COMPOSITION EXAMPLE 1 OF THE INVENTION

| QUESTION ASKED | POSITIVE RESPONSE (%) |
|---|---|
| Warms on Contact | |
| Excellent | 25.12 |
| Very Good | 31.88 |
| Good | 24.64 |
| Total | 81.64 |
| Feels Warm | |
| Excellent | 30.88 |
| Very Good | 28.92 |
| Good | 25.98 |
| Total | 85.78 |
| Does Not Feel Cold | |
| Excellent | 54.37 |
| Very Good | 29.61 |
| Good | 10.19 |
| Total | 94.53 |

As set forth in Table 3 above, 81.64% of the subjects registered a positive response that the product "warms on contact", 85.78% subjects felt that the product "feels warm" while 94.53% subjects registered that the product "does not feel cold".

EXAMPLE 5

Comparison of Lubricity

Ahmad et al. in U.S. Pat. No. 6,139,848, which is hereby incorporated herein by reference, describe a method to test lubricity of various personal lubricants known to the trade. In the described test method, the lubricity of various marketed personal lubricants was determined over a period of 300 seconds (5 minutes). The lubricity data disclosed in this patent indicates that K-Y Liquid® lubricant had a higher lubricity and was longer lasting during the 300 seconds test period than the competitive products.

Figure 5:
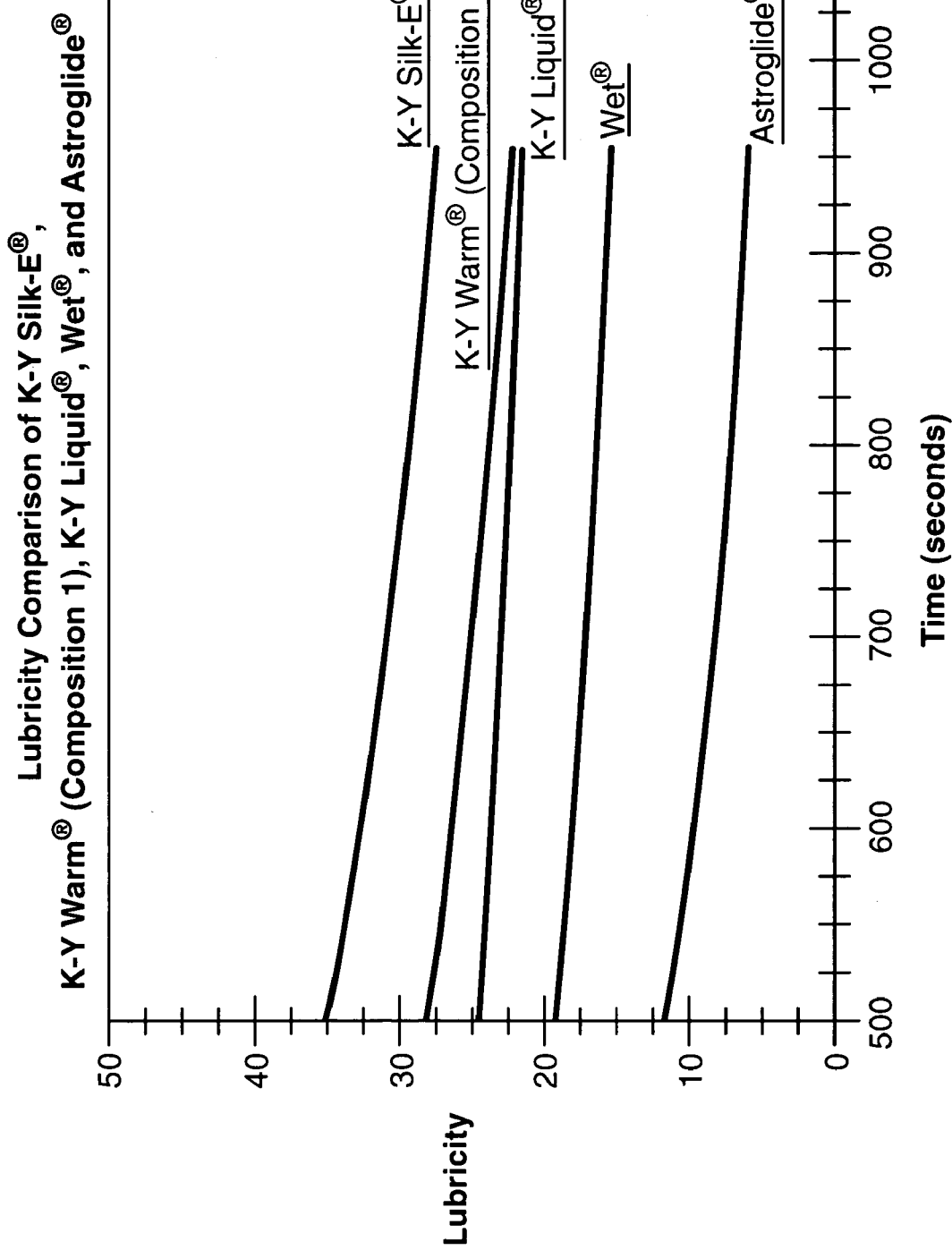
FIG. 5 is a graph comparing the Lubricity vs Time (Seconds) of the composition of Example 1 and three leading Personal Lubricants on the market.

The lubricity data set forth in U.S. Pat. No. 6,139,848 has a negative (−) sign during the "push" and positive (+) sign during the "pull" phase of the experiment. Compositions of this invention were tested using the lubricity test set forth in U.S. Pat. No. 6,129,848. However, the test duration was successfully extended to 16 minutes (960 seconds) and the data was treated to "curve-fit" to eliminate the negative (−) sign. The lubricity data for the composition 1 of this invention is compared with the data for K-Y Liquid in FIG. 5. The data indicate that Composition 1 of this invention has a higher lubricity as compare to K-Y Liquid® and that Composition 1 maintains the high lubricity for an extended period of 16 minutes (960 minutes) and is therefore longer lasting.

EXAMPLE 6

Heat of Solution

The warming effect of the compositions of this invention is believed to be caused by generating heat of solution, as opposed to creating the conditions for exothermic reactions. Exothermic reactions result in evolution of heat due to a chemical reaction between two chemicals and are uncontrolled. Such an exothermic chemical reaction may generate new products or chemical entities, some of which may not be suitable for human tissues. In contrast, when a solution is formed there is an energy change because of the difference between the forces of attraction of unlike and like molecules. Specifically, bonds are broken between molecules of the each component being mixed and new bonds are formed between neighboring molecules of the product mixture or solution. This mechanism is different from a Heat of Reaction because there is no chemical rearrangement of the constituent atoms to form products from reactants. As can be seen from the following experiment, maximum heat generated or the maximum rise in temperature is no more than 18.8° F., which makes these compositions very mild and safe.

The solution process for the compositions of this invention (COMPOSITION 15 of Example 9 below) in, for example, vaginal fluids ("X $H_2O$") can be represented by the following physical equation:

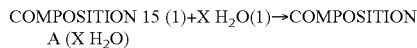

COMPOSITION 15 (1)+X $H_2O$(1)→COMPOSITION A (X $H_2O$)

The designation "COMPOSITION 15 (X $H_2O$)" represents that the product is a solution of 1 (mol) of COMPOSITION 15 in X (mol) of $H_2O$. Thus, using COMPOSITION 15, a composition according to this invention, as a personal lubricant does not change the existing amount of naturally occurring vaginal fluids. It simply forms a solution with them.

Figure 6:
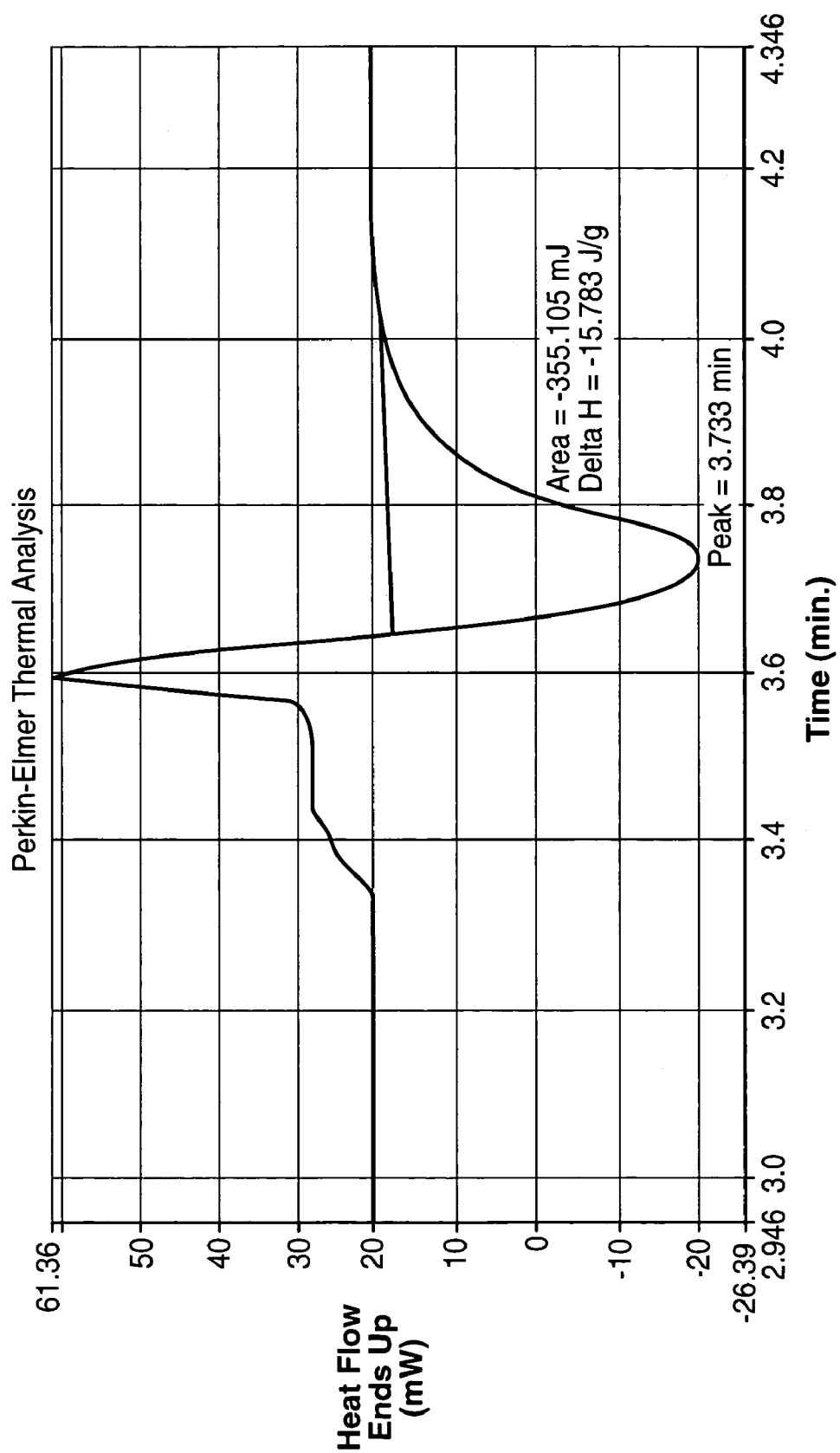
FIG. 6 is a graph depicting the results of a Differential Scanning Calorimetry experiment.
Figure 7:
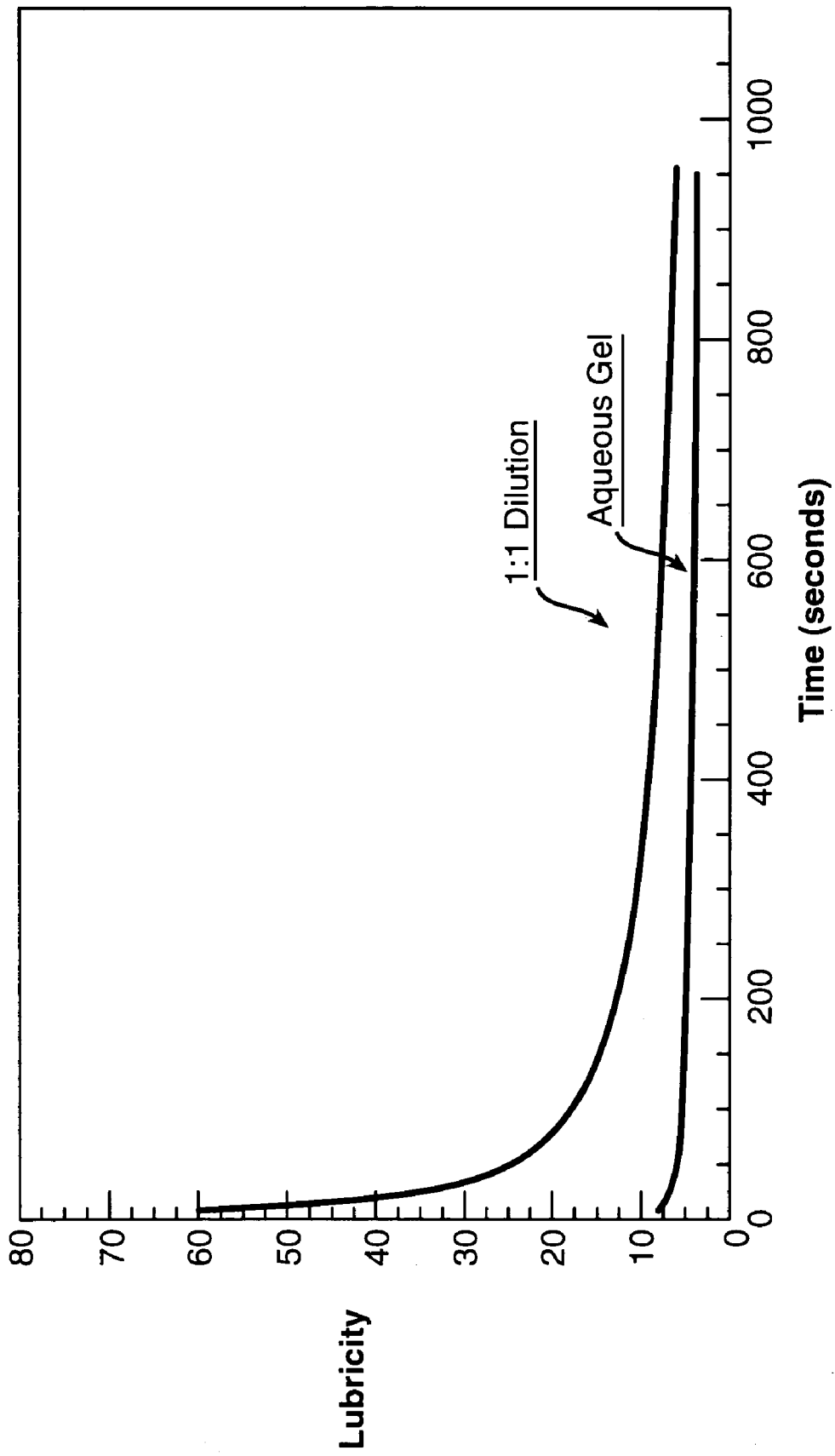
FIG. 7 is a graph comparing the Lubricity vs Time (seconds) of the composition of 1:1 Dilution vs. Aqueous Gel.
Figure 8:
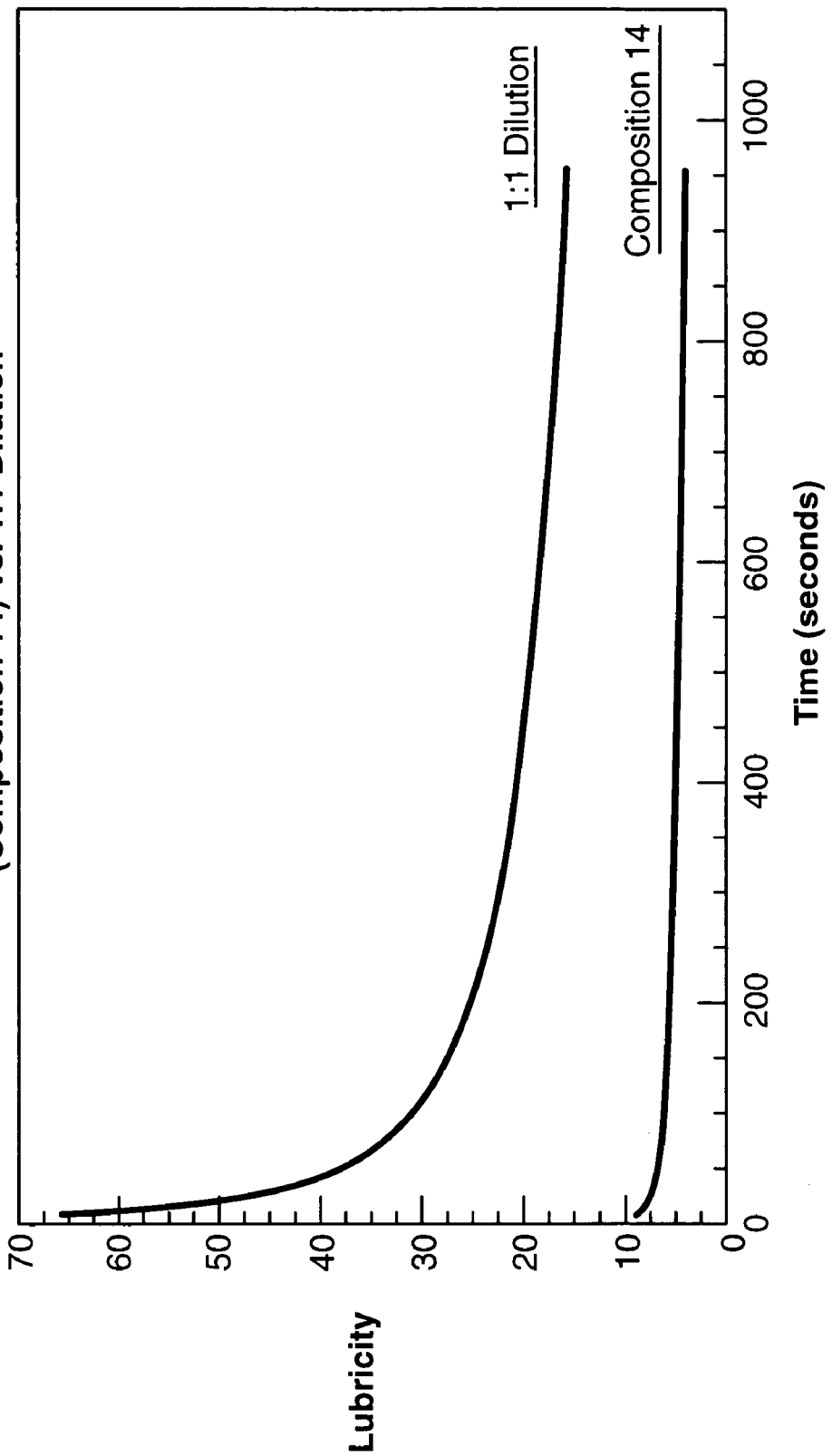
FIG. 8 is a graph comparing the Lubricity vs Time (seconds) of the composition of 1:1 Dilution vs. Composition 14.
Figure 9:
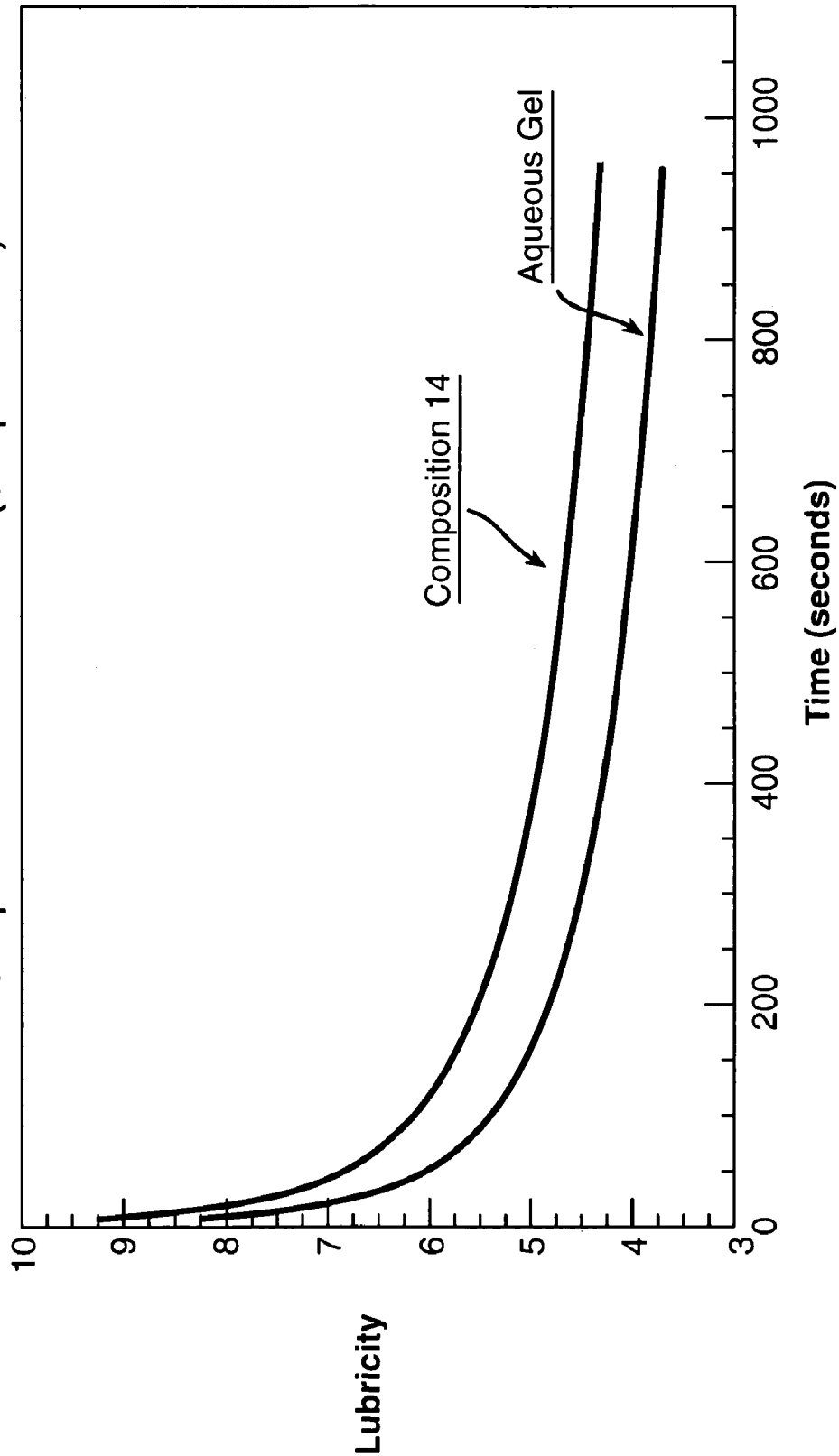
FIG. 9 is a graph comparing the Lubricity vs Time (seconds) of the composition of Composition 14 vs. Aqueous Gel.

The maximum temperature increase possible from the generation of heat by use of the compositions of this invention may be measured using thermodynamic principles. For example, Differential Scanning Calorimetry (DSC) was employed to characterize the heat released by the compositions of this invention when they come into contact with water to form a solution. In this testing, the energy released when a thin film of a particular composition was applied to a thin film of water was measured. The results of a typical test are presented in FIG. 6. The area of the exothermic (i.e., negative) peak represents the total energy released during the formation of a solution of the composition of this invention and water. Table 1 summarizes the energy released for this series of experiments.

TABLE 1

Summary of DSC Measurements of Heat Released By COMPOSITION 15/Water

| Experiment # | Composition of the Invention (mg) | Energy Released (mJ) |
|---|---|---|
| 1 | 17.85 | 398.878 |
| 2 | 22.5 | 355.108 |
| 3 | 28.32 | 267.229 |
| Average | 22.89 | 340.405 |
| Standard Deviation | 5.25 | 67.045 |

The energy release measured by the DSC is representative of the maximum energy which would be seen on the surface of the vaginal tissue. This is because the heat flux (energy flow) into the thin film of water during the formation of the solution measured by the DSC is equivalent to the heat flux (energy flow) which would be in the fluid on the surface of the vaginal tissue. Therefore, thermodynamics can be used to calculate the maximum possible temperature rise as follows:

$$Q_{max} = C_{pm} \Delta T_{max} \quad \text{(Equation 1)}$$

where, $Q_{max}$ represents the Maximum Energy Released (or, "Maximum Energy Release Index") during contact (formation of solution) of Composition 15 and water; $C_{pm}$ represents Heat Capacity of Solution of Composition 15 and Water; and $\Delta T_{max}$ represents Maximum Temperature Rise. Thus, rearranging Equation 1, we can calculate $\Delta T_{max}$, the Maximum Temperature Rise, based upon the known or measured values of the Maximum Energy Released and the Heat Capacity of Solution of Composition 15, as follows:

$$\Delta T_{max} = Q_{max}/C_{pm} \quad \text{(Equation 2)}$$

By assuming a normal distribution, the experimental results in Table 1 can be used to arrive at a worst case estimate for the maximum value of $Q_{max}$ as follows:

$$\begin{aligned}
Q_{max} &= \{\text{Average Experimental Energy Release} + \\
&\quad 3 \times (\text{Standard Deviation of} \\
&\quad \text{Experimental Energy Release})\} / \\
&\quad (\text{Average Quantity of Composition A}) \\
&= \{(340.405 \text{ mJ}) + (3)(67.045 \text{ mJ})\} / (22.89 \text{ mg}) \\
&= (541.539 \text{ mJ}/22.89 \text{ mg})
\end{aligned} \quad \text{(Equation 3)}$$

(Using this as the upper limit represents the 99.73% upper confidence limit for the normal distribution.)

In the case of $C_{pm}$, the smaller of the $C_p$ for Composition 15 and the $C_p$ for Water can be used to arrive at a worst case estimate for its minimum value. Since, $$C_p \text{ (Composition 15)} = 0.54 \text{ cal}/(g\text{-}° C.)$$

$$C_p \text{ (Composition 15)} = 1.00 \text{ cal}/(g\text{-}° C.)$$

then, $$C_{pm} \text{ (worst case minimum)} = 0.54 \text{ cal}/(g\text{-}° C.) \quad \text{(Equation 4)}$$

Therefore, a worst case estimate of the maximum temperature increase possible from the generation of heat by for Composition 15 can be arrived at by using the combining Equations 2, 3, and 4 as follows:

$$\begin{aligned}
\Delta T_{max} &= Q_{max}/C_{pm} \\
&= ((541.539 \text{ mJ})/(22.89 \text{ mg}))/ \\
&\quad (0.54 \text{ cal}/(g\text{-}°C.) \times 0.23901 \text{ cal}/J) \\
&= 10.5 \, °C. \text{ or } = 18.8 \, °F.
\end{aligned}$$

Thus, the maximum heat released upon use of Composition 15 is, at the most, about 10.5° C. or 18.8° F., a relatively small increase in heat, indicating that the temperature increase effected by the compositions of this invention are safe and comfortable to the user.

EXAMPLE 7

Generation of Warmth

Compositions 10, 11 and 12 were tested in accordance with the following procedure to determine the extent to which said compositions generate warmth upon mixture with water. Data was generated by mixing 20 ml of each composition with 20 ml of water. The temperature of the composition and that of water were recorded before water was added to the composition After the addition of water the contents were mixed for two minutes and the actual temperature was recorded. The results are set forth in the following Table:

Generation of Warmth (Rise in Temperature ° F.) Data by Mixing Equal Quantity of Each Composition with Water

| Product Name | Temperature of the Product (° F.) | Temperature of Water (° F.) | Average Expected Temperature (° F.) | Actual Temperature (° F.) | Rise in Temperature (° F.) (Expected Minus Actual) |
|---|---|---|---|---|---|
| Rise In Temperature For Compositions For Compositions Of The Invention | | | | | |
| Composition 10 | 73.00 | 70.3 | 71.6 | 87.3 | 15.7 |
| Composition 11 | 73.00 | 70.3 | 71.6 | 83.2 | 11.6 |
| Composition 12 | 73.00 | 70.3 | 71.6 | 87.1 | 15.5 |
| Rise In Temperature For The Individual Components Of The Compositions | | | | | |
| Polyethylene Glycol 400 | 72.0 | 71.0 | 71.5 | 88.5 | 17.0 |
| Propylene Glycol | 72.4 | 71.0 | 71.7 | 85.2 | 13.5 |
| Glycerin | 69.0 | 71.0 | 70.0 | 79.0 | 9.0 |

We calculated the rise in temperature For Compositions 10, 11 and 12:

Composition 10
Propylene Glycol (38% of 13.5)=5.13
Polyethylene Glycol 400 (61.5% Of 17.0)=10.45
Total: 15.58° F.

Composition 11
For Composition 11 the calculated Rise in Temperature is 15.58° F.

Composition 12
For Composition 12 the calculated Rise in Temperature is 15.15° F.

The calculated temperature for all three compositions is very close to the Actual Rise in Temperature.

EXAMPLE 8

Compositions of the Invention

The following compositions of this invention were made as follows: first, propylene glycol and glycerin were mixed. A preservative and the insulating agent were then added to the mixture in the same container. The mixture was then heated to from about 35° C. to about 45° C. to completely dissolve the preservative. The mixture was then cooled.

| Composition 1: | |
|---|---|
| Propylene Glycol | 50.00% |
| Glycerin | 45.00% |
| Honey | 5.00% |

| Composition 2: | |
|---|---|
| Propylene Glycol | 50.00% |
| Glycerin | 20.00% |
| Isopropyl Myristate | 27.00% |
| Polysorbate 60 | 3.00% |

| Composition 3: | |
|---|---|
| Propylene Glycol | 95.00% |
| Honey | 5.00% |

| Composition 4: | |
|---|---|
| Propylene Glycol | 50.00% |
| Glycerin | 20.00% |
| Isopropyl Myristate | 29.50% |
| Klucel HF | 0.50% |

| Composition 5: | |
|---|---|
| Propylene Glycol | 99.50% |
| Klucel HF | 0.50% |

| Composition 6: | |
|---|---|
| Propylene Glycol | 49.80% |
| Glycerin | 45.00% |
| Honey | 5.00% |
| Preservative | 0.20% |

| Composition 7: | |
|---|---|
| Miconazole Nitrate | 2.00% |
| Propylene Glycol | 49.80% |
| Glycerin | 43.00% |
| Honey | 5.00% |
| Preservative | 0.20% |

| Composition 8: | |
|---|---|
| Fluconazole | 2.00% |
| Propylene Glycol | 49.80% |
| Glycerin | 43.00% |
| Honey | 5.00% |
| Preservative | 0.20% |

| Composition 9: | |
|---|---|
| Metronidazole | 3.00% |
| Propylene Glycol | 49.80% |
| Glycerin | 42.00% |
| Honey | 5.00% |
| Preservative | 0.20% |

| Composition 10 (Gel): | |
|---|---|
| Propylene Glycol | 38.00 |
| Polyethylene Glycol 400 | 61.05 |

-continued

| | |
|---|---|
| Lactic Acid | 00.20 |
| Hydroxypropylcellulose | 0.75 |
| Composition 11 (Jelly): | |
| Propylene Glycol | 37.00 |
| Polyethylene Glycol 400 | 61.05 |
| Lactic Acid | 00.20 |
| Hydroxypropylcellulose | 1.75 |
| Composition 12 (Gel): | |
| Propylene Glycol | 48.00 |
| Polyethylene Glycol 400 | 51.30 |
| Lactic Acid | 0.20 |
| Hydroxypropylcellulose | 0.50 |
| Composition 13 (Jelly): | |
| Propylene Glycol | 48.55 |
| Polyethylene Glycol 400 | 50.00 |
| Lactic Acid | 0.20 |
| Hydroxypropylcellulose | 1.25 |
| Composition 14 (Jelly: | |
| Propylene Glycol | 98.55 |
| Lactic Acid | 0.20 |
| Hydroxypropylcellulose | 1.25 |
| Composition 15 (Jelly): | |
| Polyethylene Glycol 400 | 98.55 |
| Lactic Acid | 0.20 |
| Hydroxypropylcellulose | 1.25 |
| Composition 16 (Gel): | |
| Polyethylene Glycol 400 | 99.50 |
| Lactic Acid | 0.20 |
| Hydroxypropylcellulose | 0.30 |
| Composition 17 (Gel): | |
| Propylene Glycol | 74.50 |
| Glycerin | 25.00 |
| Lactic Acid | 0.20 |
| Hydroxypropylcellulose | 0.30 |
| Composition 18 (Gel): | |
| Propylene Glycol | 74.50 |
| Polyethylene Glycol 400 | 25.00 |
| Lactic Acid | 0.20 |
| Hydroxypropylcellulose | 0.30 |
| Composition 19 (Gel): | |
| Propylene Glycol | 69.50 |
| Polyethylene Glycol 400 | 15.00 |
| Glycerin | 15.00 |
| Lactic Acid | 2.00 |
| Hydroxypropylcellulose | 0.30 |
| Composition 20 (Jelly): | |
| Propylene Glycol | 73.55 |
| Polyethylene Glycol 400 | 25.00 |
| Lactic Acid | 0.20 |
| Hydroxypropylcellulose | 1.25 |
| Composition 21: | |
| Propylene Glycol | 47.80 |
| Polyethylene Glycol 400 | 48.00 |
| Hydroxypropylcellulose (Klucel HF) | 2.00 |
| Lactic acid | 0.20 |
| Miconazole Nitrate | 2.00 |
| Composition 22: | |
| Propylene Glycol | 35.00 |
| Polyethylene Glycol 400 | 60.80 |
| Hydroxypropylcellulose (Klucel HF) | 2.00 |
| Lactic acid | 0.20 |
| Miconazole Nitrate | 2.00 |
| Composition 23: | |
| Propylene Glycol | 48.80 |
| Polyethylene Glycol 400 | 48.00 |
| Hydroxypropylcellulose (Klucel HF) | 2.00 |
| Miconazole Nitrate | 2.00 |
| Composition 24: | |
| Propylene Glycol | 47.80 |
| Polyethylene Glycol 400 | 46.00 |
| Hydroxypropylcellulose (Klucel HF) | 1.00 |
| Polyvinylpyrilidone (K29-32) | 3.00 |
| Lactic acid | 0.20 |
| Miconazole Nitrate | 2.00 |
| Composition 25: | |
| Propylene Glycol | 48.80 |
| Polyethylene Glycol 400 | 48.00 |
| Hydroxypropylcellulose (Klucel HF) | 2.00 |
| Itraconazole | 2.00 |

EXAMPLE 10

In Vitro Testing for Antibacterial and Antifungal Activity

In Vitro Time-Kill Studies were used to test the antibacterial and antifungal activity of the compositions of this invention. A battery of vaginal anaerobes known to cause bacterial vaginal infections (BV), *Candida albicans* which is responsible for vulvovaginal candidiasis (VVC) and strains of *lactobacilli* were used to determine the length of contact time required to inhibit and kill these test organisms. The results of this test are summarized in Table 3. The results show that Compositions 1, 2 and 3 of the invention kill the BV causing bacteria and *Candida albicans* in 0 hour or almost instantaneously.

Surprisingly the compositions of the invention did not have any adverse effect on lactobacilli that continued to grow even after 24 hours. These results show that the compositions of this invention will be effective to treat both the fungal and bacterial vaginal infections and are selective enough not to harm *lactobacilli*.

TABLE 3

Results of In Vitro Evaluation: Activities of Compositions of the Invention

| | EXAMPLE | | | | |
|---|---|---|---|---|---|
| Organism | Composition 21 | Composition 22 | Monistat 3 Vaginal Cream | Composition 23 | MetroGel-Vaginal |
| *Gardnerella vaginalis* | 0 | 0 | 0 | 0 | 2 |
| *Gardnerella vaginalis* | 0 | 0 | 0 | 0 | 4 |
| *Gardnerella vaginalis* | 0 | 0 | 0 | 0 | >9<23 |
| *Gardnerella vaginalis* | 0 | 0 | 2 | 1 | >9<23 |

TABLE 3-continued

Results of In Vitro Evaluation: Activities of Compositions of the Invention

| Organism | Composition 21 | Composition 22 | Monistat 3 Vaginal Cream | Composition 23 | MetroGel-Vaginal |
|---|---|---|---|---|---|
| *Peptostreptococcus magnus* | 4 | 3 | 6 | 7 | 0 |
| *Peptostreptococcus magnus* | 4 | 8 | 5 | >7<23 | 0 |
| *Peptostreptococcus magnus* | 1 | 3 | 4 | 1 | 0 |
| *Peptostreptococcus tetradius* | 0 | 0 | 1 | 1 | 0 |
| *Peptostreptococcus tetradius* | 0 | 0 | 1 | 1 | 0 |
| *Peptostreptococcus tetradius* | 0 | 0 | 2 | 1 | 0 |
| *Peptostreptococcus asaccharolyticus* | 0 | 0 | 2 | 1 | 0 |
| *Peptostreptococcus asaccharolyticus* | 0 | 0 | 2 | 0 | 0 |
| *Peptostreptococcus asaccharolyticus* | 0 | 0 | 1 | 2 | 0 |
| *Prevotella bivia* | 0 | 0 | 1 | 1 | 0 |
| *Prevotella bivia* | 0 | 0 | 1 | 1 | 0 |
| *Prevotella bivia* | 0 | 0 | 1 | 1 | 0 |
| *Prevotella disiens* | 0 | 0 | 1 | 0 | 0 |
| *Prevotella disiens* | 0 | 0 | 1 | 0 | 0 |
| *Prevotella disiens* | 0 | 0 | 1 | 0 | 0 |
| *Prevotella intermedia* | 0 | 0 | 1 | 0 | 0 |
| *Prevotella intermedia* | 0 | 0 | 1 | 0 | 0 |
| *Prevotella melaninogenica* | 0 | 0 | 1 | 0 | 0 |
| *Prevotella melaninogenica* | 0 | 0 | 1 | 0 | 0 |
| *Mobiluncus mulieris* | 0 | 0 | >24 | 0 | 1 |
| *Mobiluncus mulieris* | 0 | 0 | | 0 | 3 |
| *Lactobacillus plantarum* | 0 | 0 | | 1 | 0 |
| *Lactobacillus species* | 4 | 8 | | 3 | >8<23 |
| *Lactobacillus acidophilus* | >24 | >24 | | >24 | >24 |
| *Lactobacillus acidophilus* | >24 | >24 | | >24 | 24 |
| *Candida albicans* | 0 | 0 | | 0 | >8<23 |
| *B. fragilis* | 1 | 0 | | 1 | 0 |
| *B. theta* | 0 | 1 | | 0 | 0 |

What is claimed is:

1. A substantially anhydrous lubricant composition comprising at least one polyhydric alcohol, which increases in temperature by at least about 5° C. upon exposure to moisture and which has an Energy Release Index of at least about 11 mJ/mg and wherein said polyhydric alcohol is selected from the group consisting of: glycerin, alkylene glycol, polyethylene glycol, PEGylated compounds, block copolymers comprising polyalkylene glycol and a mixture thereof and wherein said polyethylene glycol is selected from the group consisting of polyethylene glycol 300, polyethylene glycol 400 and a mixture thereof and further comprising an insulating agent having high bulk properties selected from the group consisting of honey, isopropyl myristate and isopropyl palmitate.

2. A composition according to claim 1 wherein said composition further comprises a local anesthetic.

3. A substantially anhydrous lubricant composition comprising from about 80% to about 98% by weight polyhydric alcohol and from about 1 to about 5% by weight insulating agent selected from the group consisting of honey, isopropyl myristate and isopropyl palmitate and less than about 5% by weight water.

4. A composition according to claim 3 wherein said composition comprises from about 80% to about 98% by weight polyhydric alcohol and from about 1 to about 5% by weight insulating agent selected from the group consisting of honey, isopropyl myristate and isopropyl palmitate and less than about 1% by weight water.

5. A method of treating vulvodynia comprising applying a composition comprising at least one polyol and an analgesic agent, which increases in temperature by at least about 5° C. upon exposure to moisture and which has an Energy Release Index of at least about 11 mJ/mg to a skin or mucosal surface.

6. A method of treating frostbite comprising applying a composition comprising at least one polyol, which increases in temperature by at least about 5° C. upon exposure to moisture and which has an Energy Release Index of at least about 11 mJ/mg to skin on a frostbitten extremity.

7. A method of treating dysmenorrhea comprising applying a composition comprising at least one polyol and an anti-inflammatory agent, which increases in temperature by at least about 5° C. upon exposure to moisture and which has an Energy Release Index of at least about 11 mJ/mg to a tampon and inserting said tampon vaginally.

8. A substantially anhydrous lubricant composition consisting essentially of at least one polyol, which increases in temperature by at least about 5° C. upon exposure to moisture and which has an Energy Release Index of at least about 11 mJ/mg wherein said composition further comprises a bioadhesive agent.

9. A substantially anhydrous lubricant composition comprising at least one polyhydric alcohol, which increases in temperature by at least about 5° C. upon exposure to moisture and which has an Energy Release Index of at least about 11 mJ/mg and wherein said polyhydric alcohol is selected from the group consisting of: glycerin, alkylene glycol, polyethylene glycol, PEGylated compounds, block copolymers comprising polyalkylene glycol and a mixture thereof and wherein said polyethylene glycol is selected from the group consisting of polyethylene glycol 300, polyethylene glycol 400 and a mixture thereof, said composition further comprising an insulating agent having high bulk properties selected from the group consisting of honey, isopropyl myristate and isopropyl palmitate.

10. A composition according to claim 9 wherein said composition further comprises a local anesthetic.

11. A substantially anhydrous lubricant composition consisting essentially of at least one polyol and a bioadhesive agent said composition increasing in temperature by at least about 5° C. upon exposure to moisture and which has an Energy Release Index of at least about 11 mJ/mg.

* * * * *